US012797409B2

(12) United States Patent
Gordts et al.

(10) Patent No.: US 12,797,409 B2
(45) Date of Patent: Nov. 17, 2026

(54) HEPARAN SULFATE MIMETICS TO IMPROVE GLUCOSE CLEARANCE

(71) Applicants: The Regents of the University of California, Oakland, CA (US); Philip L.S.M. Gordts, San Diego, CA (US); Kamil Godula, La Mesa, CA (US); Ryan Porell, La Jolla, CA (US); Sean Cameron Purcell, San Diego, CA (US); Greg Trieger, San Diego, CA (US)

(72) Inventors: Philip L.S.M. Gordts, San Diego, CA (US); Kamil Godula, La Mesa, CA (US); Ryan Porell, La Jolla, CA (US); Sean Cameron Purcell, San Diego, CA (US); Greg Trieger, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 476 days.

(21) Appl. No.: 18/569,174

(22) PCT Filed: Jun. 10, 2022

(86) PCT No.: PCT/US2022/033080

§ 371 (c)(1),
(2) Date: Dec. 11, 2023

(87) PCT Pub. No.: WO2022/261480

PCT Pub. Date: Dec. 15, 2022

(65) Prior Publication Data

US 2024/0293443 A1 Sep. 5, 2024

Related U.S. Application Data

(60) Provisional application No. 63/209,833, filed on Jun. 11, 2021.

(51) Int. Cl.

| | |
|---|---|
| ***A61K 31/737*** | (2006.01) |
| ***A61K 47/54*** | (2017.01) |
| ***A61K 47/59*** | (2017.01) |
| ***A61K 47/64*** | (2017.01) |

(52) U.S. Cl.

CPC .......... *A61K 31/737* (2013.01); *A61K 47/549* (2017.08); *A61K 47/595* (2017.08); *A61K 47/643* (2017.08)

(58) Field of Classification Search

None

See application file for complete search history.

(56) References Cited

U.S. PATENT DOCUMENTS

| | | | | |
|---|---|---|---|---|
| 10,792,327 | B2 * | 10/2020 | Stupp | A61L 27/48 |
| 2017/0145084 | A1 | 5/2017 | Lavallie et al. | |
| 2019/0358296 | A1 | 11/2019 | Jonker et al. | |

FOREIGN PATENT DOCUMENTS

| | | | |
|---|---|---|---|
| WO | WO-2022261480 | A1 | 12/2022 |

OTHER PUBLICATIONS

International Application Serial No. PCT/US2022/033080, International Search Report mailed Oct. 28, 2022, 7 pgs.

International Application Serial No. PCT/US2022/033080, Invitation to Pay Additional Fees mailed Aug. 25, 2022, 3 pgs.

International Application Serial No. PCT/US2022/033080, Written Opinion mailed Oct. 28, 2022, 8 pgs.

Trieger, et al., "Glycocalyx engineering with heparan sulfate mimetics attenuates Wnt activity during adipogenesis to promote glucose uptake and metabolism", bioRxiv preprint, [Online]. Retrieved from the Internet: <URL: https://www.biorxiv.org/content/1 0.1101/2021.07.08.45171 Ov1.full.pdf>, (Jul. 9, 2021), 1-44 pgs.

Zhang, et al., "Heparan sulfate assists SARS-CoV-2 in cell entry and can be targeted by approved drugs in vitro", bioRxiv preprint, [Online]. Retrieved from the Internet: <URL: https://www.biorxiv.org/content/10.1101/2020.07.14.202549v2.full.pdf>, (Sep. 18, 2020), 1-39 pgs.

International Application Serial No. PCT/US2022/033080, International Preliminary Report on Patentability mailed Dec. 21, 2023, 10 pgs.

* cited by examiner

*Primary Examiner* — Dale R Miller

(74) *Attorney, Agent, or Firm* — SCHWEGMAN LUNDBERG & WOESSNER, P.A.

(57) ABSTRACT

Described herein are compositions and methods for increasing glucose uptake of differentiated adipocytes using heparan sulfate mimetics comprising a polymer backbone comprising sulfated di saccharides, the polymer backbone linked to a cell membrane anchoring portion, wherein the heparan sulfate mimetic associates with the cell membrane or binds to membrane surface proteins of the pre-adipocytes and the adipocytes.

20 Claims, 19 Drawing Sheets

Specification includes a Sequence Listing.

D0A0

D2A6

D2S6

HEPARAN SULFATE MIMETICS TO IMPROVE GLUCOSE CLEARANCE

CROSS-REFERENCE TO RELATED APPLICATION

This application is a U.S. National Stage Filing under 35 U.S.C. 371 from International Application No. PCT/US2022/033080, filed on Jun. 10, 2022, and published as WO 2022/261480 A1 on Dec. 15, 2022, which claims the priority of U.S. provisional application Ser. No. 63/209,833, filed Jun. 11, 2021, the disclosure of each of which is incorporated herein by reference in its entirety.

INCORPORATION BY REFERENCE OF SEQUENCE LISTING

This application contains a Sequence Listing which has been submitted electronically in ST25 format and hereby incorporated by reference in its entirety. Said ST25 file, created on Jul. 17, 2026, is named 1133098US1.txt and is 4,096 bytes in size.

FEDERAL FUNDING

This invention was made with government support under DK063491 and HD087954 awarded by the National Institutes of Health. The government has certain rights in the invention.

BACKGROUND

Type 2 diabetes is a growing global health problem caused by excess caloric intake, reduced energy, and the resulting onset of obesity. The constant nutrient influx associated with a Western diet result in high frequency of elevated blood glucose levels. This hyperglycemia demands a continuous insulin secretion from pancreatic beta cells to ensure glucose uptake for energy production and storage. The continuous insulin secretion will desensitize its perception by adipocytes, where glucose is normally stored in the form of lipids. This insulin resistance coincides with the onset of type 2 diabetes, leading ultimately to beta cell failure. Type 2 diabetes patients have a high risk to develop neuropathy, retinopathy, cardiovascular disease, stroke, and poor outcomes when coping with infectious disease. Overall, this greatly reduces their of quality of life and life expectancy. As a result, type 2 diabetes has been a prominent focus of medical research to find effective treatments. Current treatment strategies focused on increasing insulin perception, augmenting oxidative tissue activity or decreasing excessive food consumption or nutrient absorption, have been limited by poor efficacy or detrimental side-effects as exemplified by the COVID-19 pandemic.

Adipose tissue plays a crucial role in maintaining metabolic homeostasis by storing lipids and glucose from circulation as intracellular fat. Adipose tissue adapts to nutritional excess by expansion through increasing cell size (hypertrophy) or cell number (hyperplasia). To allow those changes, the extracellular matrix (ECM) surrounding adipocytes undergoes constant remodeling. It thereby influences the adipocyte's potential for expansion, regulates signal transduction, and provides an area for interactions with other cells and molecules.

The ECM plays a critical role in cellular adhesion, migration, proliferation, and differentiation. While ECMs of most mammalian cells share similar components, such as collagen fibers, membrane proteins, and glycoproteins, the relative abundance of those components changes with a cell's specificity and metabolic function. Abnormal deposition of ECM components, such as collagens, CD44 and osteopontin, is a hallmark of obesogenic adipocytes; hence, the ECM is associated with restrictions in adipocyte expansion promoting fibrosis which results in metabolic dysfunction and inflammation. Therefore, a need exists for agents that can modulate the ECM of adipocytes to improve metabolic function and reduce insulin sensitivity.

SUMMARY

Compositions and methods are described herein that are useful for the treatment of metabolic diseases, such as type 2 diabetes. The compositions and methods include the use of a heparan sulfate (HS) mimetic comprising a polymer backbone comprising sulfated disaccharides, the polymer backbone linked to a cell membrane anchoring portion. When inserted into a glycocalyx of adipocyte cell membranes, the HS mimetic provides increased insulin-dependent glucose clearance. HS proteoglycans are polysaccharide chains comprised of repeating units of N-acetylglucosamine (GlcNAc) and glucuronic acid (GlcA), which are enzymatically modified through N-deacetylation, epimerization at the uronic acid residue, and sulfation. These modifications produce domains with negatively charged residues, which are selectively recognized by HS-binding proteins. Defects in lipid accumulation in differentiated adipocytes lacking Syndecan-1, also an HS proteoglycan (HSPG), or the HS biosynthetic enzyme, N-acetylglucosamine N-deacetylase-N-sulfotransferase 1 (NDST1), have been attributed to decreased endocytosis of triglyceride-rich lipoproteins.

The compositions described herein can include a heparan sulfate mimetic for targeting pre-adipocytes and adipocytes comprising: a polymer backbone comprising sulfated disaccharides, the polymer backbone linked to a cell membrane anchoring portion, wherein the heparan sulfate mimetic associates with the cell membrane or binds to membrane surface proteins of the pre-adipocytes and the adipocytes. The methods described herein can include increasing glucose uptake by differentiated adipocytes comprising: incubating pre-adipocytes with a composition comprising a polymer backbone comprising sulfated disaccharides, the polymer backbone linked to a cell membrane anchoring portion. These compositions and methods are useful for improving glucose uptake capacity and metabolic utilization in terminally differentiated adipocytes.

DESCRIPTION OF THE FIGURES

Aspects of the present disclosure can be better understood with reference to the following drawings. The components in the drawings are not necessarily to scale. Instead, emphasis is placed on clearly illustrating the principles of the present disclosure. Furthermore, components can be shown as transparent in certain views for clarity of illustration only and not to indicate that the illustrated component is necessarily transparent.

FIG. 1A is an Oil Red O stain of differentiated WT and Ndst1$^{-/-}$ adipocytes treated with or without heparin (100 μg/ml). Nuclei were visualized with 4',6-diamidino-2-phenylindole (DAPI) fluorescent stain. FIG. 1D shows RNAseq quantification of adipogenesis marker Dlk2. FIG. 1E shows RNAseq quantification of adipogenesis marker Cebpb. FIG. 1F shows RNAseq quantification of adipogenesis marker Cebpd. FIG. 1G shows RNAseq quantification of adipogenesis marker Glut4. FIG. 1H shows RNAseq quantification of adipogenesis markerAp2. FIG. 1I shows RNAseq quantification of adipogenesis marker Foxo3. FIG. 1J shows RNAseq quantification of adipogenesis marker Fas. FIG. 1K shows RNAseq quantification of adipogenesis marker Zbtb16. FIG. L shows cell surface binding of Very low-density lipoprotein (VLDL) binding to the WT and $Ndst1^{-/-}$ cells (n=3). FIG. M shows lipoprotein lipase (LPL) binding to WT or $Ndst1^{-/-}$ adipocytes treated with or without heparin (100 μg/ml) (Two-way ANOVA, n=3). FIG. N shows radiolabeled fatty acid 9,10-[$^3$H(N)]-Palmitate uptake in WT or $Ndst1^{-/-}$ adipocytes treated with or without heparin (100 μg/ml) (Two-way ANOVA, n=3). Data are presented as mean±s.d., **P<0.0001, *P<0.001, **P<0.01, *P<0.05.

FIG. 2A is a schematic showing HS mimetic bearing heparan sulfate glycosaminoglycan (HS GAG) disaccharide repeats incorporated into the membranes of differentiating MEFs. The schematic shows Wnt ligand sequestration by cell membrane anchored HS glycopolymers. FIG. 2B is shows chemical structures of selected HS GAG disaccharides D2A6 (disulfated) D2S6 (trisulfated) and DOA0 (unsulfated). FIG. 2C is a graph of Wnt5a binding activity assessed by ELISA with D2S6 glycopolymer (EC50=5.1 nM, $r^2$=0.94, n=3) or heparin (EC50=28.2 nM, $r^2$=0.87, n=3), showing dose-dependent binding activity. FIG. 2D is a graph of Wnt10b binding activity assessed by ELISA with D2S6 HS mimetics (EC50=5.1 nM, $r^2$=0.97, n=2) or heparin (EC50=30.1 nM, $r^2$=0.95, n=3), showing dose-dependent binding activity. FIG. 2E is a graph showing 3[H]-2-deoxy-glucose uptake by $Ndst1^{-/-}$ (upper panel) and WT (lower panel) MEFs treated with various HS GAG glycopolymers. The MEFs were treated with the indicated HS mimetics (DOA0, D2A6, or D2S6) for one hour at 37° C. on day 0 to 3 of adipocyte differentiation. HS mimetics D2A6 and D2S6 dose-dependently enhance $^3$[H]-2-deoxy-glucose uptake in differentiated adipocytes (day 6) (Two-way ANOVA, n=3). FIG. 2F is a graph showing glucose (upper panel) and lactate (lower panel) concentration of media of HS mimetic treated $Ndst1^{-/-}$ adipocytes (day 6) using YSI analysis. Cells treated with the HS mimetics show a dose response rescue of glucose utilization (lowered media concentration) and increased production of the glycolysis product lactate (Two-way ANOVA, n=2). Data are presented as mean±s.d., *P<0.0001, *P<0.001, **P<0.01.

FIG. 4A is a schematic illustrating EMCs expressing an Alpl aptamer target. An embryonic HS mimetic containing a DNA aptamer targeting unit and a bioactive HS domain are added to the EMCs, which facilitate FGF2 binding to its cognate cell surface receptor FGFR. Activation of MAPK activity results in subsequent differentiation of EMCs to neural progenitor cells (NPCs). FIG. 4B is a graph depicting corrected total cell fluorescence (CTCF) of $Ext1^{-/-}$ mouse embryonic stem cells expressing embryonic markers Oct4, Alpl, and Sox1 over 6 days of differentiation. Over the course of differentiation, expression of embryonic markers Oct4 and Alpl quickly declined, and was difficult to detect beyond Day 3. Sox1, conversely, began to express on Day 3 and robust expression was observed by Day 6 of differentiation. This data indicates that expression of Sox1 on Day 4 of differentiation is an efficient measure of the efficacy of HS-aptamer chimeras to promote neural differentiation as Sox1 is approaching maximum CTCF intensity. FIG. 4C shows images of cells with fluorescent signals from expressed Oct4, Alpl, and Sox on days 1, 3, and 6 of differentiation. Sox1 shows maximal fluorescence on Day 6 of differentiation.

FIG. 5A illustrates the chemical reaction for preparing heparin that is pre-functionalized at the reducing end with biotin over two steps to produce biotinylated heparin (approximately 20% functionalized). FIG. 5B is a schematic of an assembly of the HS glycopolymer linked to Streptavidin-$AF_{488}$, which is linked to the aptamer that binds ALPL (abbreviated as Hep-SA-19S). The Hep-SA-Apt conjugate is in 1:1:1 stoichiometry produced by sequential addition of biotinylated heparin (5 equiv.) and biotinylated aptamer (1 equiv.).

FIG. 6A is a graph illustrating that Hep-SA-19S bound to the $Ext1^{-/-}$ cell surface, as determined by flow cytometry after 40 min incubation in suspension, with an observed EC50 of 70 nM while Hep-SA-Scr control and Hep-SA alone did not result in significant cell surface binding. FIG. 6B shows a graph illustrating embryonic stage-specificity of Hep-SA-19S insertion into the glycocalyx of mouse embryonic stem cells that were subjected to neural differentiation protocols until Day 6 in the presence of soluble heparin at a concentration of 5 ug/mL.

FIG. 7A is a flow cytometry scatter plot showing that $Ext1^{-/-}$ mouse embryonic stem cells lacking cell surface HS do not bind FGF2. Populations of mouse embryonic stem cells were plotted by mean fluorescent intensity (MFI)

(Hep-SA-19S, AF488) and MFI (FGF2, AF647) and show remodeling of the cell surface and Hep-SA-19S dependent FGF2 binding after treatment with Hep-SA-19S at 100 nM. A modest increase in FGF2 activity was observed in the absence of conjugate due to non-specific FGF2 antibody staining. Hep-SA-19S shows an increase in both AF488 and AF647 fluorescence over Hep-SA-Scr and Hep-SA alone, indicating binding of Hep-SA-19S to the cell surface and enhanced association of FGF2 with the bound Hep-SA-19S. FIG. 7B is a graph showing FGF2 binding activity increases as a function of cell-surface bound conjugate. The presence of the scrambled control Scr aptamer sequence reduces non-specific binding of Hep-SA at all concentrations evaluated (0-100 nM) and a control lacking FGF2 shows minimal background signal, except in the presence of Hep-SA where nonspecific antibody binding was observed.

FIG. 8A shows a workflow for neoPG synthesis using recombinant or tissue purified GAGs. Fluorogenic bifunctional azidocoumarin sulfonyl fluoride (ACS-F) linker was conjugated via the sulfur (IV) fluoride exchange reaction to GAG chains primed at their reducing end with reactive amines. Subsequent strain-promoted azide-alkyne cycloaddition (SPAAC) reaction with cyclooctyne-functionalized BSA (BCN-BSA) furnished the desired neoPGs. Fluorescence signal produced upon conversion of the ACS handle into triozolylcoumarin sulfonamide (TCS) was used to monitor the progress of the conjugation reaction. FIG. 8B is a graph showing absorbance (dashed) and fluorescence (solid) spectra of quenched ACS-F (black) and unquenched TCS-BSA (green). FIG. 8C shows the effects of neoPG degradation by specific GAG-lyases (red) on protein binding. Hep7-BSA treated with heparin lyases and probed for FGF2 binding. CS12-BSA treated with chondroitinase ABC and probed for CS-56 antibody binding. KS6-BSA treated with keratanase II and probed for 5D4 antibody binding. HA7-BSA treated with hyaluronidase and probed for CD44 binding. (Bar graphs represent n=3 replicates, p-values were determined using student's t-test, $p<0.01$, *$p<0.001$, ****$p<0.001$).

DETAILED DESCRIPTION

Figure 1A:
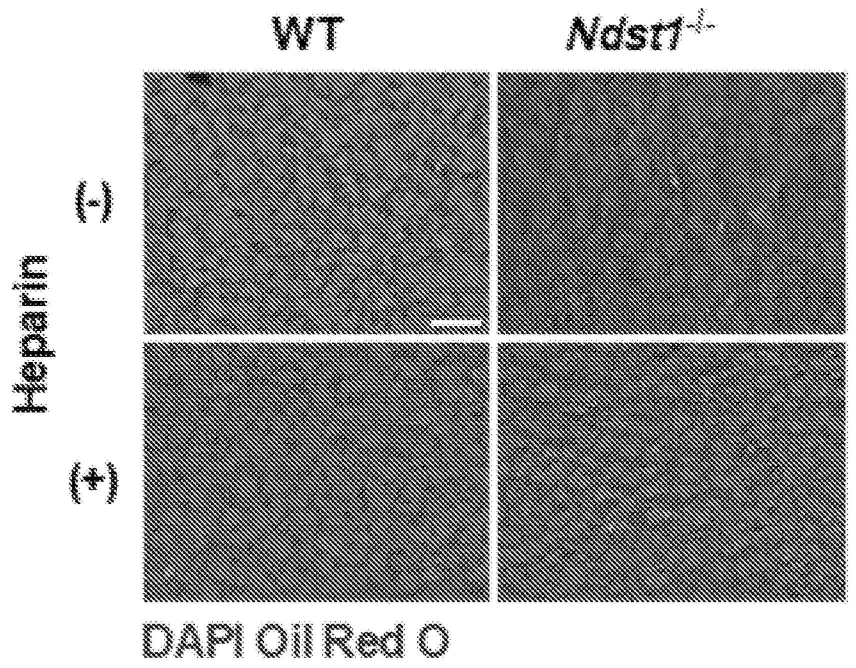
FIGS. 1A-N illustrate how cell surface heparan sulfate regulates lipid storage in differentiating adipocytes.

Compositions, methods, and kits are described herein for making and using a heparan sulfate (HS) mimetic. Compositions can include a HS mimetic comprising: a polymer backbone comprising sulfated disaccharides, the polymer backbone linked to a cell membrane anchoring portion. Methods can include methods for increasing glucose uptake by differentiated adipocytes comprising incubating pre-adipocytes with a composition comprising a polymer backbone comprising sulfated disaccharides, the polymer backbone linked to a cell membrane anchoring portion. In some aspects, such compositions and methods are useful for remodeling the glycocalyx of newly generated fat tissues to increase their overall cellular metabolism and glucose demand, independently of insulin driven glucose uptake.

The HS mimetics disclosed herein can target Wnt signaling. This metabolic phenotype occurs when pre-adipocytes are treated with the HS mimetics early in the process of adipogenesis. Transcriptomic analysis revealed that Wnt signaling was most perturbed in response to HS modulation within a differentiation window. For example, the HS mimetics can target Wnt signaling when pre-adipocytes are treated within the first day, two (2) days, three (3) days, four (4) days, five (5) days, or six (6) days of adipogenesis. In another example, the pre-adipocytes can be treated with the HS mimetics each day for the first two (2) days, three (3) days, four (4) days, five (5) days, or six (6) days of adipogenesis. The pre-adipocytes treated can be in a mixed population of pre-adipocytes in different stages of adipogenesis or in a mixed population of pre-adipocytes and adipocytes.

Cell surface HS can both promote and inhibit cell signaling events via either promoting signaling complex formation or by sequestering ligands away from cognate receptors, respectively. Eliminating cell surface HS activity in pre-adipocytes leads to enhanced Wnt signaling, pointing to an inhibitory role of endogenous cell surface HS in Wnt regulation. This conclusion is further supported by the restoration of the wildtype phenotype, upon application of small molecule inhibitors of Wnt signaling such as those described herein. Additionally, the protein backbone of a subclass of glypicans, including GPC4, can bind the lipid moiety of palmitoylated Wnt; serving as a ligand sequestering depot before being handed over to cognate receptors. Mutual binding of the lipid moiety to the GPC4 core protein and the interaction of protein moiety with GPC4 HS chains increases its Wnt binding affinity and promote sequestration.

The compositions and methods disclosed herein augment the cellular glycocalyx with synthetic HS mimetics that exhibit Wnt sequestering activity. The HS mimetics can be based on synthetic poly(acrylamide) chains, a Wnt binding domain composed of HS disaccharides carrying N-, 2-O, 3-O, and 6-O sulfation and a 1,2-dihexadecanoyl-sn-glycero-3-phosphoethanolamine (DPPE) lipid for membrane targeting. This approach can provide a robust enhancement of glucose uptake in both HS-deficient and WT adipocytes after differentiation.

The heparan sulfate mimetic can have the formula:

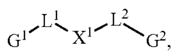

wherein $G^1$ comprises the sulfated disaccharides, $L^1$ and $L^2$ are each linkers, $X^1$ is a polymer, and $G^2$ is the cell membrane anchoring portion. $G^1$ can comprise groups of the formula

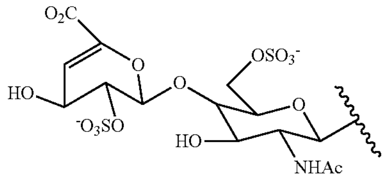

or

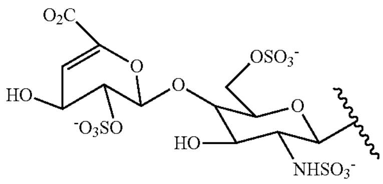

wherein the wavy line represents the point of attachment of $G^1$ to $L^1$. $X^1$ can be poly(acrylamide) of the formula

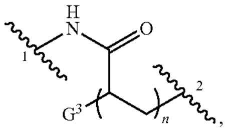

wherein $G^3$ is a reporter group or is absent, the wavy line with the numeral 1 represents the point of attachment to $L^1$ and the wavy line with the numeral 2 represents the point of attachment to $L^2$. $L^1$ can be an alkyl or an alkyl-O— group. $L^2$ can comprise an amido group of the formula $-G^4-C(O)N-$, wherein $G^4$ represents an alkyl group. $L^2$ can further comprise a group of the formula $-G^4-OP(O)_2O-$. $G^2$ can be a lipid, an aptamer, an antibody, an antibody fragment or a protein.

The heparan sulfate mimetic can have the formula:

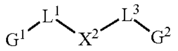

wherein $G^1$ comprises the sulfated disaccharides, $L^1$ is a linker, $L^3$ is a linker or absent, $X^2$ comprises a protein, and $G^2$ is the cell membrane anchoring portion. $X^2$ can comprise streptavidin bound to biotin groups conjugated to $L^1$ and $L^3$. $X^2$ can be a group of the formula $-X^3-G^5-X^4-$, wherein $X^3$ and $X^4$ each represent a biotin group and $G^5$ represents streptavidin. $G^2$ can be a lipid, an aptamer, an antibody, an antibody fragment or a protein.

For example, structures of synthetic HS mimetics contemplated herein include HS mimetics of the formula (I):

(I)

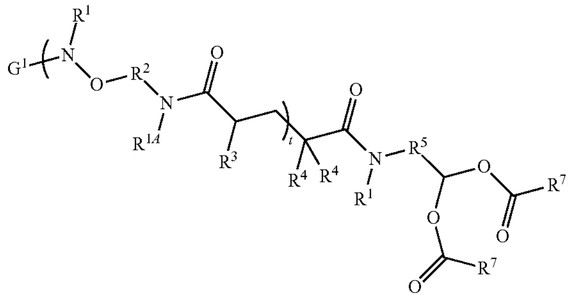

wherein:

t is an integer from 1 to 1000 (e.g., from about 1 to about 500, 50 to about 160, about 100 to about 300, about 150 to about 250, about 100 to about 200, about 75 to about 150; about 200 to about 300, about 150 to about 175, 175 to about 225, or about 275 to about 325, from about 250 to about 650);

$G^1$ is

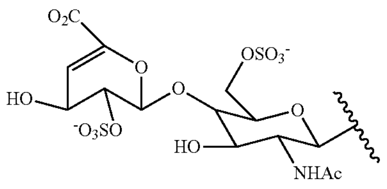

or

-continued

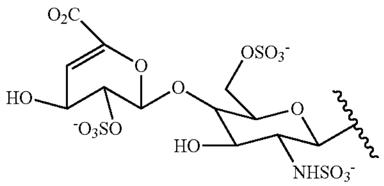

;

each $R^1$ and $R^4$ is independently H or alkyl;

$R^2$ is alkylene;

$R^3$ is H or a reporter moiety;

each $R^4$ is independently H or alkyl;

$R^5$ is alkylene optionally interrupted by an $-OP(O_2)-O-$ group; and each $R^7$ is, independently a $(C_{10}-C_{30})$ alkyl group.

Examples of HS mimetics of the formula (I) include compounds of the formula (II):

(II)

D0A0

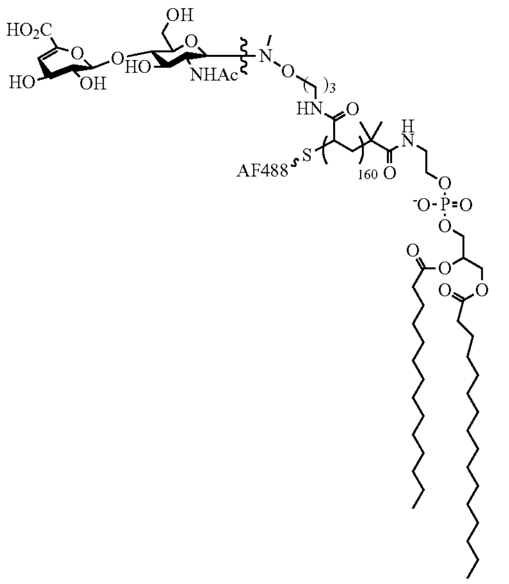

D2S6

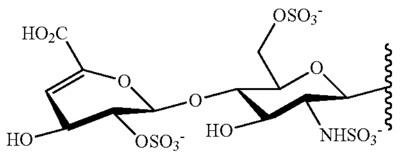

D2A6

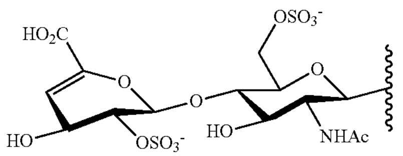

-continued

AF488

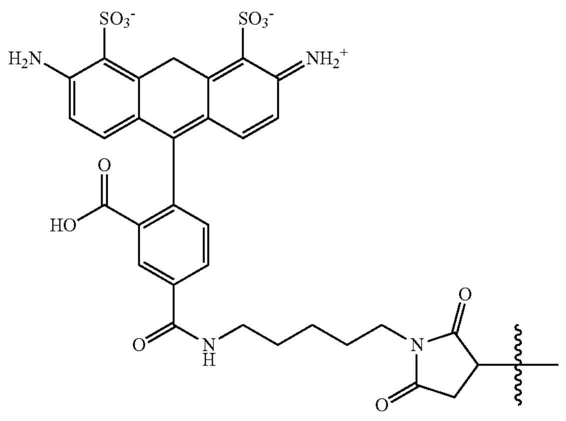

Structure D0A0 shows a HS mimetic that includes an unsulfated dissacharide used as a control in the Examples below. Structure D2S6 shows a trisulfated dissacharide. Structure D2A6 shows a disulfated dissacharide. Either structure D2S6 or structure D2S6 can replace the unsulfated dissacharide of structure D0A0. Structure D0A0 also includes an example of a cell membrane anchoring portion comprising a phospholipid. Structure AF488 is a maleimide reporter for monitoring the efficiency (% of poly(acrylamide) linker molecules occupied by dissacharides) of side chain modification of poly(acrylamide) with dissacharides using UV-Vis and NMR, though other reporter moieties are also contemplated herein, including cyanine dyes (e.g., Cy5, Cy7, and the like) and other Alexa Fluor dyes (e.g., Alexa Fluor 350, 405, 532, 546, and the like). The sulfated dissacharides composition of the HS mimetics D0A0, D2A6, and D2S6, is as follows as shown in Table 1:

TABLE 1

| HS-MIMETIC | % AF488 | % GLYCAN |
|---|---|---|
| D2S6 | 86 | 43 |
| D2A6 | 86 | 75 |
| D0A0 | 86 | 88 |

Accordingly, HS mimetics are contemplated herein wherein the HS mimetics comprise glycan in a range from about 30% to about 95% glycan, about 35% to about 90%, about 40% to about 85%, about 43% to about 75%, about 45% to about 70%, about 50% to about 65%, about 55% to about 60%, or about 100% as a function of available sites on the polymer backbone. Thus, for example, in the context of compounds of the formula (II), if t is 100 and the % glycan is 40, that means that 40 out of the 100 possible side groups (e.g. nitrogen, oxygen, or carbon atoms) that could be connected to G', in fact, have a $G^1$ connected to them. In another example, monomers containing the glycans can be polymerized and can result in HS mimetics comprising % glycan of about 100%.

In Ndst1-deficient pre-adipocytes, treatment with the HS mimetics resulted in a 100% improved glucose uptake (FIG. 2E) capacity above the basal levels in untreated WT adipocytes. This indicates a comparable or better ability of the HS-mimetics to attenuate HS mediated signaling compared to endogenous HS in WT cells. In WT cells a somewhat lower but still robust improvement is observed in glucose uptake by approximately 50%. This outcome is consistent with less efficient incorporation of the sulfated HS-mimetics presumably due to increased electrostatic shielding from endogenous HS structures in WT cells. Remodeling the glycocalyx with the HS mimetics can alter adipogenesis to improve glucose metabolism and clearance in newly differentiated adipocytes.

Polymer Backbone

The HS Mimetic can include a polymer backbone comprising sulfated disaccharides, such as those of formula (I) and (II). In some cases, the polymer backbone can be a poly(acrylamide) scaffold decorated with pendant N-methylaminooxy groups, which are reactive toward the hemiacetal functionality of the reducing glycans. In some aspects, the polymer backbones can be substantially linear. The polymer can be any suitable length including from approximately one hundred (100) to approximately three hundred (300) acrylamide molecules long. The molecular weight of the polymer backbone can be, for example, approximately 7,000 g/mol to approximately 21,000 g/mol.

In various aspects, the sulfated disaccharides can be sulfated glycosaminoglycan (GAG), on chemically sulfated non-GAG reducing disaccharides, such as lactose, maltose, or a combination thereof. Synthesis of sulfated GAGs incorporated into a poly(acrylamide) scaffold is disclosed in Huang, et. al., Glycocalyx Remodeling with Proteoglycan Mimetics Promotes Neural Specification in Embryonic Stem Cells, *J. Am. Chem. Soc.* 136: 10565-10568 (2014), which is incorporated herein in its entirety.

Sulfation of the disaccharides increases the glucose uptake activity of the HS mimetic, as the non-sulfated control HS mimetic (D0A0) showed only a limited ability to improve glucose uptake by the adipocytes. See FIG. 2C. For example, the disaccharides can be disulfated (D2A6) or trisulfated (D2S6). See FIG. 2B. WT adipocytes treated with the HS mimetic having disulfated disaccharides improved basal glucose uptake capacity by 39%. WT adipocytes treated with the HS mimetic having trisulfated disaccharides improved basal glucose uptake capacity by 47%. The sulfated glycosaminoglycan disclosed herein can be synthesized as described in Huang, M. L., et. al. Glycocalyx Remodeling with Proteoglycan Mimetics Promotes Neural Specification in Embryonic Stem Cells, *J. Am. Chem. Soc.* (2014) 136: 10565-10568.

Sulfated GAGs are polysaccharide chains appended to a protein core of proteoglycans that are abundant on cell surfaces. The GAG polysaccharides are bound to the protein core via a glycosidic bond to serine and threonine residues. Sulfated GAGs can be classified according to their monosaccharide composition as heparan sulfate (HS), chondroitin sulfate (CS), dermatan sulfate (DS), and keratan sulfate (KS). Hyaluronan (HA), which is the last member of the GAG family, lacks sulfation and is not attached to proteins.

The biological specificity of GAGs is established during their biosynthesis through a non-templated process via a sequence of enzymatic modifications, which elongate the individual polysaccharide chains and install negatively charged sulfate groups. This results in structurally complex sulfation patterns organized in domains along the polysaccharides that provide high affinity binding sites for proteins.

Cell Membrane Anchoring Portion

The HS mimetic can further comprise a cell membrane anchoring portion linked to the polymer backbone comprising the sulfated disaccharides. the activity of the HS mimetic is related to its anchoring in the cell membrane because supplementation with soluble heparin has no effect on cellular glucose uptake. See FIG. 2C-D. The cell membrane anchoring portion can comprise any suitable molecule(s)

that can insert or intercalate into a cell membrane or attach to molecules that are attached or embedded into the cell membrane of pre-adipocytes. For example, the cell membrane anchoring portion can include, but is not limited to, a hydrophobic lipid, a glycolipid, a hydrophobic octadecyl alkane, a cholesterol derivative, cholesterols, sterols, phospholipid, a transmembrane protein, a peptide, an amphipathic molecule, an aptamer, a protein, an antibody, or an antibody CDR. In some cases, the cell membrane anchoring portion may include non-polymer molecules that bind to the outside of liposomes or cell membranes such as haptens, antibodies and nanobodies, receptor ligands, enzymes, cytokines, peptides, and hormones that provide the desired cell surface recognition feature.

In some aspects, the cell membrane anchoring portion can comprise a hydrophobic lipid that inserts into the cell membrane. The hydrophobic lipid can be any lipid that can spontaneously insert into lipid bilayers, such as cell membranes. For example, the hydrophobic lipid can comprise 1,2-dihexadecanoyl-sn-glycero-3-phosphoethanolamine (DPPE), 1,2-distearoyl-sn-glycero-3-phosphorylethanolamine, (DSPE), cholesterol, glycerolipids, synthetic lipids, or ceramides.

Antibodies (cdr)

In some aspects, the cell membrane anchoring portion can comprise an antibody or an antigen-binding portion of an antibody. The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The antibody or an antigen-binding portion of an antibody can recognize a pre-adipocyte cell surface marker. The cell surface marker can be a cell surface protein expressed in pre-adipocytes but not mature differentiated adipocytes. The cell surface marker can also be a cell surface protein expressed in more abundance in pre-adipocytes as compared to mature differentiated adipocytes. For example, the cell surface marker can be Pref-1, PDGFα, or adiponectin. The antibody or an antigen-binding portion can be conjugated to the heparan sulfate mimetic through known methods of making antibody-drug conjugates, including cross-linking and utilizing labile linkers.

Aptamer

In some aspects, the cell membrane anchoring portion can include an aptamer. Aptamers are small nucleic acid structures that exhibit highly selective affinity for a target. Their ability to target protein biomarkers makes them useful for cell-specific or cell stage-specific delivery. Aptamer targets can include target proteins on a surface of a cell membrane of a pre-adipocyte. Cell stage-specific aptamers can bind a cell surface protein that is present on the cell surface of pre-adipocytes in greater quantity as compared to differentiated adipocytes or cell surface proteins that are present on pre-adipocytes, but substantially absent from differentiated adipocytes. For example, aptamers targeting pre-adipocytes can bind cell surface PDGFα or adiponectin.

Liposomal Fusion with Cell Membrane

The HS mimetic can be prepared with a liposome for targeted delivery to cell membranes. Liposomes may comprise concentric bilayers of phospholipids, wherein the HS mimetic is inserted into the bilayer. The liposomes can fuse with cell membranes to deliver the membrane embedded HS mimetic to treated cells. The liposomes can include various stabilizers such as polyethylene glycol to improve circulation times and prevent liposomal uptake by the reticuloendothelial system upon administration to an animal.

Dosages, Formulations and Routes of Administration

Pharmaceutical formulations containing the therapeutic agents described herein can be prepared by available procedures using available ingredients. The formulations can contain pharmaceutically acceptable carriers, vehicles and adjuvants. For example, the therapeutic agents can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive pharmaceutical carriers such as kaolin and bentonite can be added. Lubricants such as talc, calcium and magnesium stearate, and solid polyethylene glycols can also be included. Preservatives can also be added. The compositions of the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible, for example, to prepare solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

As noted above, preservatives can be added to help maintain the shelve life of the dosage form. The active agents and other ingredients can form suspensions, solutions, or emulsions in oily or aqueous vehicles, and can contain formulatory agents such as suspending, stabilizing and/or dispersing agents. Alternatively, the therapeutic agents and other ingredients can be in powder form, obtained by aseptic isolation of sterile solid or by lyophilization from solution, for constitution with a suitable vehicle, e.g., sterile, pyrogen-free water, before use.

The compositions can also include antioxidants, surfactants, preservatives, film-forming, keratolytic or comedolytic agents. Antioxidants such as t-butylhydroquinone, butylated hydroxyanisole, butylated hydroxytoluene and α-tocopherol and its derivatives can be added.

The compositions can include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

Furthermore, the active ingredients can also be used in combination with other therapeutic agents, for example, pain relievers, anti-inflammatory agents, anti-cancer agents and the like, whether for the conditions described or some other condition.

Kits

The present invention further pertains to a packaged pharmaceutical composition such as a kit or other container for detecting, controlling, preventing or treating a disease. The kits of the invention can be designed for detecting, controlling, preventing or treating metabolic diseases such as those described herein (e.g., diabetes).

In one embodiment, the kit or container can hold the heparan sulfate mimetic at least partially encapsulated in a biodegradable material, such as, as well as instructions for preparing a composition that includes the heparan sulfate mimetic.

In another embodiment, the kit or container can hold a therapeutically effective amount of a pharmaceutical composition for treating, preventing or controlling a disease and instructions for using the pharmaceutical composition for control of the disease. The pharmaceutical composition can include at least one type of heparan sulfate mimetic in a therapeutically effective amount such that the disease is controlled, prevented or treated. Such a composition can be in liquid form, powder form or other form permitting ready administration to a patient.

The kits of the invention can also comprise containers with tools useful for administering the compositions of the invention. Such tools include syringes, swabs, catheters, antiseptic solutions and the like.

Some kits can include all of the desired tools, solutions, compounds, including mixing vessels, utensils, and injection devices, to treat a patient according to any of the methods described herein. In one embodiment, a kit includes liposomes of the various embodiments described herein. The liposomes can be sterile-packaged as a dry powder in a suitable container (e.g., a substantially water-impermeable) such as a syringe, vial (e.g., the vial can include a septum and/or a crimp seal; and the vial can optionally comprise an inert atmosphere, such as a nitrogen atmosphere or dry air) or pouch (e.g., a pouch comprising a moisture barrier; and the pouch can optionally comprise an inert atmosphere, such as a nitrogen atmosphere, or dry air). The kit can also include a desiccant. The desiccant can be included in the pouch or integrated into the layers of the pouch material. In some embodiments, the microspheres can be sterile-packaged in frozen vehicle. As mentioned previously, the vehicle can be any suitable vehicle, including flowable vehicles (e.g., a liquid vehicle) such as a flowable, bioresorbable polymer, saline, sterile water, Ringer's solutions, and isotonic sodium chloride solutions. Examples of vehicles include, but are not limited, to Sodium Chloride Injection USP (0.9%), Ringer's Injection USP, Lactated Ringer's Injection USP, Sodium Lactate Injection USP, Dextrose Injection USP (5% or 10%), Bacteriostatic Water for Injection USP and Sterile Water for Injection USP. In some examples, the microspheres can be suspended in water; pre-filled into a container, such as a syringe; and frozen.

The kit can include at least one static mixing element, such as a one that is attached to a syringe. In some embodiments, the user provides a static mixing element to deliver the microspheres.

The kit can also include beads that serve to, among other things, disaggregate any liposome agglomeration that can occur when the microspheres of the various embodiments described herein are reconstituted with a vehicle. In some embodiments, the beads are sufficiently larger than the microspheres, so that the microspheres can be selectively delivered to the injection site, while the beads remain in the injection device (e.g., a syringe). For example, the beads can have at least one dimension that is about 1 mm. The beads can be of any suitable shape, including spherical and oval in shape. The beads can also have any suitable texture. For example, the beads can have a smooth texture and/or a rough texture. The beads can also be made of any suitable material, including glass, ceramic, metal (e.g. stainless steel), polymeric (e.g. ePTFE or polypropylene), and composite materials. The beads can be included in the kit in a separate container; in the same container as the microspheres of the various embodiments described herein; or the user can provide beads of suitable size, shape, texture, and/or materials at the point of care.

The kit can also include an injection vehicle described herein, such as sterile water or sterile saline (e.g., in the case where the target injection area is substantially hydrophobic or lipophilic) or other suitable vehicle, including a non-aqueous vehicle (e.g., a hydrophobic, liquid vehicle described herein). Prior to administration, the microspheres can be added to the injection vehicle to form a suspension and agitated (e.g., stirred, shaken or vortexed) to maximize homogeneity. In some embodiments, the microspheres can come in the kit, suspended in a vehicle, such as a non-aqueous vehicle (e.g., a hydrophobic, liquid vehicle described herein).

The kit can further include a hypodermic needle or other delivery device, such as a cannula, catheter or other suitable tubing. The kit can further include instructions, dosage tables, and other pertinent information for a practitioner.

The kit can include one or more additional APIs (e.g., a local anesthetic) either in the same container as the microspheres of the various embodiments described herein or in a separate container, such that the API in a separate container can be combined with the microspheres and vehicle to provide a bolus of an API upon administration (e.g., injection) of the microspheres. In other embodiments, the user can provide one or more additional APIs that can be combined with the heparan sulfate mimetic of the various embodiments described herein, at the point of care.

The kits can include instructions or printed indicia, to provide for directions for reconstituting the contents of the multiple packages, and/or for the administration of the resulting composition (e.g., the injectable compositions). For example, instructions on printed indicia can instruct injection into biological tissue including at least one of fatty tissue, epidural tissue, and at or near a targeted nerve.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "alkyl" as used herein refers to substituted or unsubstituted straight chain, branched or cyclic, saturated mono-valent groups having from 1 to 20 carbon atoms, 10 to 20 carbon atoms, 12 to 18 carbon atoms, 6 to 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of straight chain mono-valent ($C_1$-$C_{20}$)-alkyl groups include those with from 1 to 8 carbon atoms such as methyl (i.e., $CH_3$), ethyl, n-propyl, n-butyl, n-pentyl, n-hexyl, n-heptyl, n-octyl groups. Examples of branched mono-valent ($C_1$-$C_{20}$)-alkyl groups include isopropyl, iso-butyl, sec-butyl, t-butyl, neopentyl, and isopentyl. Examples of cyclic alkyl groups include cyclopropyl, cyclobutyl, cyclopently, cyclohexyl, cyclooctyl, bicyclo[1.1.1]pentyl, bicyclo[2.1.1]hexyl, bicyclo[2.2.1]heptyl, and adamantyl. Cycloalkyl groups further include substituted and unsubstituted polycyclic cycloalkyl groups such as, but not limited to, norbornyl, adamantyl, bornyl, camphenyl, isocamphenyl, and carenyl groups, and fused rings such as, but not limited to, decalinyl, and the like. For example cycloalkyl includes an adamantyl substituted by one, two, three, four, or more substituents, for example, at the tertiary bridgehead positions at the methylene bridges. In some embodiments, alkyl includes a combination of substituted and unsubstituted alkyl. As an example, alkyl, and also ($C_1$)alkyl, includes methyl and substituted methyl. As a particular example, ($C_1$)alkyl includes benzyl. As a further example, alkyl can include methyl and substituted ($C_2$-$C_5$)alkyl. Alkyl can also include substituted methyl and unsubstituted ($C_2$-$C_5$)alkyl. In some embodiments, alkyl can be methyl and $C_2$-$C_8$ linear alkyl. In some embodiments, alkyl can be methyl and $C_2$-$C_8$ branched alkyl. The term methyl is understood to be —$CH_3$, which is not substituted. The term methylene is understood to be —$CH_2$—, which is not substituted. For comparison, the term ($C_1$)alkyl is understood to be a substituted or an unsubstituted —$CH_3$ or a substituted or an unsubstituted —$CH_2$—. Representative substituted alkyl groups can be substituted one or more times with any of the groups listed herein, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkyl groups can be substituted from a set of groups including amino, hydroxy, cyano, carboxy, nitro, thio and alkoxy, but not including halogen groups. Thus, in some embodiments alkyl can be substituted with a non-halogen group. For example, representative substituted alkyl groups can be substituted with a fluoro group, substituted with a bromo group, substituted with a halogen other than bromo, or substituted with a halogen other than fluoro. In some embodiments, representative substituted alkyl groups can be substituted with one, two, three or more fluoro groups or they can be substituted with one, two, three or more non-fluoro groups. For example, alkyl can be trifluoromethyl, difluoromethyl, or fluoromethyl, or alkyl can be substituted alkyl other than trifluoromethyl, difluoromethyl or fluoromethyl. Alkyl can be haloalkyl or alkyl can be substituted alkyl other than haloalkyl.

The term "alkylenyl" as used herein refers to substituted or unsubstituted straight chain, branched or cyclic, saturated bi-valent groups having from 1 to 20 carbon atoms, 10 to 20 carbon atoms, 12 to 18 carbon atoms, 6 to 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of branched mono-valent ($C_1$-$C_{20}$)-alkyl groups include isopropyl, iso-butyl, sec-butyl, t-butyl, neopentyl, and isopentyl. Examples of straight chain bi-valent ($C_1$-$C_{20}$)alkyl groups include those with from 1 to 6 carbon atoms such as $—CH_2—$, $—CH_2CH_2—$, $—CH_2CH_2CH_2—$, $—CH_2CH_2CH_2CH_2—$, and $—CH_2CH_2CH_2CH_2CH_2—$.

The term "alkenyl" as used herein refers to substituted or unsubstituted straight chain, branched or cyclic, saturated mono- or bi-valent groups having at least one carbon-carbon double bond and from 2 to 20 carbon atoms, 10 to 20 carbon atoms, 12 to 18 carbon atoms, 6 to 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. The double bonds can be trans or cis orientation. The double bonds can be terminal or internal. The alkenyl group can be attached via the portion of the alkenyl group containing the double bond, for example, vinyl, propen-1-yl and buten-1-yl, or the alkenyl group can be attached via a portion of the alkenyl group that does not contain the double bond, for example, penten-4-yl. Where specified, the parent moiety should be understood to be attached to the alkenyl group at a vinylic position of the double bond rather than a non-vinylic position. For example, where an aromatic ring is substituted with a π-conjugated alkenyl group, it should be understood to be substituted at the vinyl position rather than a non-vinylic position. As a further example, an aromatic ring substituted with a π-conjugated propenyl group would be understood to be a propen-1-yl or a propen-2-yl group rather than a propen-3-yl group. Examples of mono-valent ($C_2$-$C_{20}$)-alkenyl groups include those with from 1 to 8 carbon atoms such as vinyl, propenyl, propen-1-yl, propen-2-yl, butenyl, buten-1-yl, buten-2-yl, sec-buten-1-yl, sec-buten-3-yl, pentenyl, hexenyl, heptenyl and octenyl groups. Examples of branched mono-valent ($C_2$-$C_{20}$)-alkenyl groups include isopropenyl, iso-butenyl, sec-butenyl, t-butenyl, neopentenyl, and isopentenyl. Examples of straight chain bi-valent ($C_2$-$C_{20}$)alkenyl groups include those with from 2 to 6 carbon atoms such as $—CHCH—$, $—CHCHCH_2—$, $—CHCHCH_2CH_2—$, and $—CHCHCH_2CH_2CH_2—$. Examples of branched bi-valent alkyl groups include $—C(CH_3)CH—$ and $—CHC(CH_3)CH_2—$. Examples of cyclic alkenyl groups include cyclopentenyl, cyclohexenyl and cyclooctenyl. For example, alkenyl can be vinyl and substituted vinyl. For example, alkenyl can be vinyl and substituted ($C_3$-$C_8$)alkenyl. Alkenyl can also include substituted vinyl and unsubstituted ($C_3$-$C_8$) alkenyl. Representative substituted alkenyl groups can be substituted one or more times with any of the groups listed herein, for example, monoalkylamino, dialkylamino, cyano, acetyl, amido, carboxy, nitro, alkylthio, alkoxy, and halogen groups. As further example, representative substituted alkenyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkenyl groups can be substituted from a set of groups including monoalkylamino, dialkylamino, cyano, acetyl, amido, carboxy, nitro, alkylthio and alkoxy, but not including halogen groups. Thus, in some embodiments alkenyl can be substituted with a non-halogen group. In some embodiments, representative substituted alkenyl groups can be substituted with a fluoro group, substituted with a bromo group, substituted with a halogen other than bromo, or substituted with a halogen other than fluoro. For example, alkenyl can be 1-fluorovinyl, 2-fluorovinyl, 1,2-difluorovinyl, 1,2,2-trifluorovinyl, 2,2-difluorovinyl, trifluoropropen-2-yl, 3,3,3-trifluoropropenyl, 1-fluoropropenyl, 1-chlorovinyl, 2-chlorovinyl, 1,2-dichlorovinyl, 1,2,2-trichlorovinyl or 2,2-dichlorovinyl. In some embodiments, representative substituted alkenyl groups can be substituted with one, two, three or more fluoro groups or they can be substituted with one, two, three or more non-fluoro groups.

The term "alkynyl" as used herein, refers to substituted or unsubstituted straight and branched chain alkyl groups, except that at least one triple bond exists between two carbon atoms. Thus, alkynyl groups have from 2 to 50 carbon atoms, 2 to 20 carbon atoms, 10 to 20 carbon atoms, 12 to 18 carbon atoms, 6 to 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. Examples include, but are not limited to ethynyl, propynyl, propyn-1-yl, propyn-2-yl, butynyl, butyn-1-yl, butyn-2-yl, butyn-3-yl, butyn-4-yl, pentynyl, pentyn-1-yl, hexynyl, Examples include, but are not limited to $—C≡CH$, $—C≡C(CH_3)$, $—C≡C(CH_2CH_3)$, $—CH_2C≡CH$, $—CH_2C≡C(CH_3)$, and $—CH_2C≡C(CH_2CH_3)$ among others.

The term "aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to 10 carbon atoms or 6 to 8 carbon atoms. Examples of ($C_6$-$C_{20}$)aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. Examples include substituted phenyl, substituted napthalenyl, substituted azulenyl, substituted biphenylyl, substituted indacenyl, substituted fluorenyl, substituted phenanthrenyl, substituted triphenylenyl, substituted pyrenyl, substituted naphthacenyl, substituted chrysenyl, and substituted anthracenyl groups. Examples also include unsubstituted phenyl, unsubstituted napthalenyl, unsubstituted azulenyl, unsubstituted biphenylyl, unsubstituted indacenyl, unsubstituted fluorenyl, unsubstituted phenanthrenyl, unsubstituted triphenylenyl, unsubstituted pyrenyl, unsubstituted naphthacenyl, unsubstituted chrysenyl, and unsubstituted anthracenyl groups. Aryl includes phenyl groups and also non-phenyl aryl groups. From these examples, it is clear that the term ($C_6$-$C_{20}$)aryl encompasses mono- and polycyclic ($C_6$-$C_2$m)aryl groups, including fused and non-fused polycyclic ($C_6$-$C_{20}$)aryl groups.

The term "heterocyclyl" as used herein refers to substituted aromatic, unsubstituted aromatic, substituted non-aromatic, and unsubstituted non-aromatic rings containing 3 or more atoms in the ring, of which, one or more is a heteroatom such as, but not limited to, N, O, and S. The term "heteroaryl" is a fully aromatic heterocyclyl and thus a subset of the term heterocyclyl. The term "heterocycloalkenyl" refers to a heterocyclyl group containing an olefin within a non-aromatic ring, such that the olefin is the point of connection to the parent moiety. A heterocyclyl group can thus be a heterocycloalkyl, heterocycloalkenyl, or a heteroaryl, or if polycyclic, any combination thereof. In some embodiments, heterocyclyl groups include 3 to 20 ring members, whereas other such groups have 3 to 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-membered ring with two carbon atoms and three heteroatoms, a 6-membered ring with two carbon atoms and four heteroatoms and so forth. Likewise, a $C_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase heterocyclyl group includes fused ring species including those that include fused aromatic and non-aromatic groups. Representative heterocyclyl groups include, but are not limited to piperidynyl, pyrrolidinyl, piperazinyl, and morpholinyl. For example, heterocyclyl groups include, without limitation:

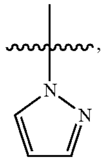,
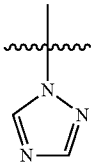,
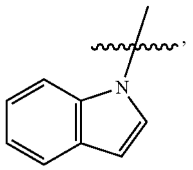,
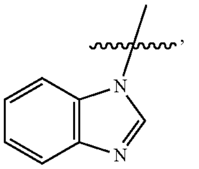,
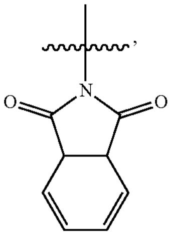,
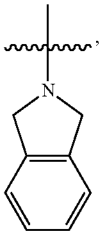,
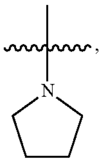,
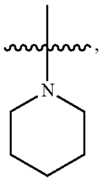,
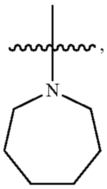,
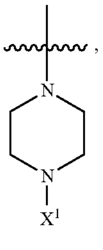, -continued

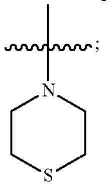; and 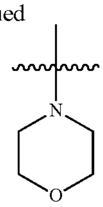, wherein $X^1$ represents H, ($C_1$-$C_{20}$)alkyl, ($C_6$-$C_{20}$)aryl or an amine protecting group (for example, a t-butyloxycarbonyl group) and wherein the heterocyclyl group can be substituted or unsubstituted. Representative heteroaryl groups include furanyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups. In some embodiments, the heteroaryl is a 5-membered heteroaryl. In some embodiments, the heteroaryl is other than pyridine, pyrimidine, pyridazine, pyrazine, or fused derivatives thereof. A π-excessive heteroaryl is a heteroaryl that is electron-rich such that it can function as an electron donating group. Examples of π-excessive heteroaryls are furan, thiophene, indole, pyrrole, benzofuran, and benzothiophene.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to 12-20 or 12-40 carbon atoms bonded to the oxygen atom, and can further include double or triple bonds, and can also include heteroatoms. Thus, alkyoxy also includes an oxygen atom connected to an alkyenyl group and oxygen atom connected to an alkynyl group. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "aryloxy" as used herein refers to an oxygen atom connected to an aryl group as are defined herein. The point of substitution to the parent moiety is at the oxygen atom.

The term "arylcarbonyl" as used herein refers to a carbonyl (CO) group connected to an aryl group as are defined herein. The point of substitution to the parent moiety is at the carbonyl group.

The term "heteroarylcarbonyl" as used herein refers to a carbonyl (CO) group connected to an heteroaryl group as are defined herein. The point of substitution to the parent moiety is at the carbonyl group.

The term and "arylalkyl" as used herein refers to alkyl groups as defined herein in which a hydrogen or carbon bond of an alkyl group is replaced with a bond to an aryl group as defined herein. Representative aralkyl groups include benzyl, biphenylmethyl and phenylethyl groups and fused (cycloalkylaryl)alkyl groups such as 4-ethyl-indanyl. Aralkenyl groups are alkenyl groups as defined herein in which a hydrogen or carbon bond of an alkenyl group is replaced with a bond to an aryl group as defined herein. The point of substitution to the parent moiety is at the alkyl group.

The terms "halo," "halogen," or "halide" group, as used herein, by themselves or as part of another substituent, mean, unless otherwise stated, a fluorine, chlorine, bromine, or iodine atom.

The term "amino" as used herein refers to a substituent of the form $—NH_2$, —NHR, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, alkenyl, alkynyl, alkoxy, aryl, cycloalkyl, heterocyclyl, group or the like.

The term "formyl" as used herein refers to a group containing an aldehyde moiety. The point of substitution to the parent moiety is at the carbonyl group.

The term "alkoxycarbonyl" as used herein refers to a group containing a carbonyl moiety wherein the group is bonded via the carbonyl carbon atom. The carbonyl carbon atom is also bonded to an oxygen atom which is further bonded to an alkyl group. Alkoxycarbonyl also includes the group where a carbonyl carbon atom is also bonded to an oxygen atom which is further bonded to an alkyenyl group. Alkoxycarbonyl also includes the group where a carbonyl carbon atom is also bonded to an oxygen atom which is further bonded to an alkynyl group. In a further case, which is included in the definition of alkoxycarbonyl as the term is defined herein, and is also included in the term "aryloxycarbonyl," the carbonyl carbon atom is bonded to an oxygen atom which is bonded to an aryl group instead of an alkyl group.

The term "alkylamido" as used herein refers to a group containing a carbonyl moiety wherein the group is bonded via the carbonyl carbon atom. The carbonyl carbon atom is also bonded to a nitrogen group which is bonded to one or more alkyl groups. In a further case, which is also an alkylamido as the term is defined herein, the carbonyl carbon atom is bonded to a nitrogen atom which is bonded to one or more aryl group instead of, or in addition to, the one or more alkyl group. In a further case, which is also an alkylamido as the term is defined herein, the carbonyl carbon atom is bonded to a nitrogen atom which is bonded to one or more alkenyl group instead of, or in addition to, the one or more alkyl and or/aryl group. In a further case, which is also an alkylamido as the term is defined herein, the carbonyl carbon atom is bonded to a nitrogen atom which is bonded to one or more alkynyl group instead of, or in addition to, the one or more alkyl, alkenyl and/or aryl group.

The term "carboxy" as used herein refers to a group containing a carbonyl moiety wherein the group is bonded via the carbonyl carbon atom. The carbonyl carbon atom is also bonded to a hydroxy group or oxygen anion so as to result in a carboxylic acid or carboxylate. Carboxy also includes both the protonated form of the carboxylic acid and the salt form. For example, carboxy can be understood as COOH or $CO_2H$.

The term "alkylthio" as used herein refers to a sulfur atom connected to an alkyl, alkenyl, or alkynyl group as defined herein. The point of substitution to the parent moiety is at the sulfur atom.

The term "arylthio" as used herein refers to a sulfur atom connected to an aryl group as defined herein. The point of substitution to the parent moiety is at the sulfur atom.

The term "alkylsulfonyl" as used herein refers to a sulfonyl group connected to an alkyl, alkenyl, or alkynyl group as defined herein. The point of substitution to the parent moiety is at the sulfonyl group.

The term "alkylsulfinyl" as used herein refers to a sulfinyl group connected to an alkyl, alkenyl, or alkynyl group as defined herein. The point of substitution to the parent moiety is at the sulfinyl group.

The term "dialkylaminosulfonyl" as used herein refers to a sulfonyl group connected to a nitrogen further connected to two alkyl groups, as defined herein, and which can optionally be linked together to form a ring with the nitrogen. This term also includes the group where the nitrogen is further connected to one or two alkenyl groups in place of the alkyl groups. The point of substitution to the parent moiety is at the sulfonyl group.

The term "dialkylamino" as used herein refers to an amino group connected to two alkyl groups, as defined herein, and which can optionally be linked together to form a ring with the nitrogen. This term also includes the group where the nitrogen is further connected to one or two alkenyl groups in place of the alkyl groups. The point of substitution to the parent moiety is at the nitrogen atom.

The term "dialkylamido" as used herein refers to an amido group connected to two alkyl groups, as defined herein, and which can optionally be linked together to form a ring with the nitrogen. This term also includes the group where the nitrogen is further connected to one or two alkenyl groups in place of the alkyl groups. The point of substitution to the parent moiety is at the amido group.

Each of the various substituent groups described herein can be substituted or unsubstituted. The term "substituted" as used herein refers to a group that is substituted with one or more groups (substituents) including, but not limited to, the following groups: deuterium (D), halogen (for example, F, Cl, Br, and I), R, OR, $OC(O)N(R)_2$, CN, NO, $NO_2$, $ONO_2$, azido, $CF_3$, $OCF_3$, methylenedioxy, ethylenedioxy, $(C_3-C_{20})$ heteroaryl, $N(R)_2$, $Si(R)_3$, SR, SOR, $SO_2R$, $SO_2N(R)_2$, $SO_3R$, $P(O)(OR)_2$, $OP(O)(OR)_2$, C(O)R, C(O)C(O)R, $C(O)CH_2C(O)R$, C(S)R, C(O)OR, OC(O)R, $C(O)N(R)_2$, C(O)N(R)OH, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, or C(=NOR)R wherein R can be hydrogen, $(C_1-C_{20})$ alkyl or $(C_6-C_{20})$aryl. Substituted also includes a group that is substituted with one or more groups including, but not limited to, the following groups: fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic ring. Such adjacent groups can have a vicinal or germinal relationship, or they can be adjacent on a ring in, for example, an ortho-arrangement. Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxycarbonyl, alkoxycarbonyl, thiophenyl, and nitrophenyl groups. In various embodiments, a substituted group may be substituted with a group other than a carbonyl-containing group, nitro, cyano, sulfinyl, sulfonyl, or a halogen-containing group. In various embodiments, a substituted group may be substituted with a group other than an electron-withdrawing group. Some substituted groups in certain embodiments may be substituted solely with one or more electron-donating groups.

EXAMPLES

Example 1: Materials and Methods

This Example describes some of the materials and methods used in the development of the HS mimetics described herein.

General Chemistry Techniques and Instrumentation

All chemicals were purchased from Sigma Aldrich and used as received unless otherwise noted. Glycans were purchased from CarboSynth (San Diego, CA) and used as received. Lipid and AlexaFluor 488-modified HS-mimetic glycopolymers GP and their polymer precursor P were prepared according to published procedures.[40] Details regarding their composition and characterization are included as Supplemental Information. HS disaccharide nomenclature was used as defined by Lawrence et al.[41] Proton nuclear magnetic resonance (H NMR) spectra were collected on a Bruker 300 MHz NMR spectrometer. Spectra are reported in parts per million (ppm) on the o scale relative to the residual solvent (CDCl3 and D20) as an internal standard. Size exclusion chromatography (SEC) was performed on a Hitachi Chromaster system equipped with an RI detector and an 8 μm, mixed bed, 300×7.5 mm cm PL aquagel-OH mixed medium column in DMF with 0.1% LiBr at 70° C. UV-Vis characterization of glycopolymers were recorded with a quartz cuvette using a ThermoScientific Nanodrop 2000c spectrophotometer.

Cell Culture

MEF cells were grown in monolayer culture in tissue culture treated T25 flasks at 37° C., 5% CO2. Cells were maintained in DMEM+glucose, +L glutamine with 10% fetal bovine serum. Cells were passaged every 3 days at a ratio of 1:10 after dissociation with 0.25% trypsin-EDTA at 37° C., 5% CO2, which was neutralized with an equal volume of growth medium. Cells were washed with PBS after the removal of old media. Cells are seeded into a 24 well plate at a density of 30,000 cells/cm$^2$. Cells are allowed to grow to confluence for 48 hours, at which point the media is switched to differentiation media (day 0).

Adipogenic Differentiation.

Cells were seeded on a 24-well plate at a density of 30,000 cells/cm$^2$. Cells were allowed to grow to confluence for 48 hours. At this point (Day 0), the media were removed, cells were washed with PBS, and differentiation media with or without heparin (100 μg/ml) were added. Differentiation media consisted of 0.1 μM dexamethasone, 450 μM 3-isobutyl-1-methylxanthine, 2 μM insulin, and 1 μM rosiglitazone in DMEM supplemented with 10% FBS. On Day 3 of differentiation, cells were washed with PBS and treated with insulin media, which consisted of 2 μM insulin, and 1 μM rosiglitazone in DMEM with 10% FBS. The cellular cholesterol and triglyceride content was determined after lysing cells in 0.1M NaOH. Total plasma cholesterol and plasma triglyceride levels (Sekisui Diagnostics) and protein levels (BCA protein assay) were determined using commercially available kits.

Adipose Tissue Stromal Vascular Cell Differentiation

Around 1 g subcutaneous WAT from 8- to 14-week-old, male or female mice was dissected, washed, minced, and digested in 1 ml DMEM containing 0.25 U/ml collagenase D (Sigma) at 37° C. with constant agitation at 200 rpm for 25-35 min. To stop the digestion, complete DMEM including 10% FBS and 1% P/S was added to the digestion mixture. Then the cells were filtered through a 100 μm cell strainer. After centrifugation at 200×g for 10 min, the floating adipocyte fraction (AF) was collected for protein isolation, while the pellet containing stromal vascular fraction (SVF) was resuspended in fresh complete medium and seeded on a 10-cm cell culture dish. At a confluency of ~80%, cells were seeded on 6- and 12-well plates and grown to confluency for differentiation. Differentiation was induced by using complete DMEM/F12 media supplemented with 1 μM dexamethasone, 0.5 mM isobutylmethylxanthine (IBMX), 5 μg/ml insulin, and 1 μM rosiglitazone. Three days after induction, medium was changed to complete DMEM/F12 supplemented with 5 μg/ml insulin for two days, afterwards cells were maintained in complete DMEM/F12 medium. On day 7, fully differentiated cells were used for experiments.

Gene Expression Analysis

Total RNA from homogenized tissue and cells was isolated and purified using E.Z.N.A. HP Total RNA (Omega) or RNeasy mini (Qiagen) kits according to the manufacturers' instructions. The quality and quantity of the total RNA was monitored and measured with NanoDrop (NanoDrop Technologies, Inc. Wilmington, DE). 5-10 ng of cDNA was used for quantitative real-time PCR with gene-specific primers (Table 2) and TBP as a house keeping gene on a BioRad CFX$^{96}$ Real-time PCR system (Bio Rad).

TABLE 1

Primers (SEQ ID NOs: 3-12)

| Gene | Forward primer (5'-3') | Reverse primer (5'-3') |
|---|---|---|
| Glut4 | CAATGGTTGGGAAGGATAGG GCTA | GTAGGGGCCAATGAGGAAC CGTC |
| aP2 | AGACCGAGATTTCCTTCAAA GTG | CCATCTAGGCTTATGATGC TCTTCA |

TABLE 1-continued

| Primers (SEQ ID NOs: 3-12) | | |
|---|---|---|
| Gene | Forward primer (5'-3') | Reverse primer (5'-3') |
| TBP | GAAGCTGCGGTACAATTCCAG | CCCCTTGTACCCTTCACCAAT |
| Pparg | GCATGGTGCCTTCGCTGA | TGGCATGTGTGTGTCAACCATG |
| Cebpb | TGGACAAGAACAGCAACGA | AATCTCCTAGTCCTGGCTTG |

RNA-Seq Library Preparation

Cells were lysed in Trizol and total RNA was extracted using the Direct-zol kit (Zymo Research, CA USA). On column DNA digestion was also performed with DNAse treatment. Stranded RNA-Seq libraries were prepared from polyA enriched mRNA using the TruSeq Stranded mRNA library prep kit (lllumina). Library construction and sequencing was performed by the University of California San Diego (UCSD) Institute for Genomic Medicine. Libraries were single-end sequenced for 76 cycles on a HiSeq 4000 to a depth of 20-30 million reads.

RNASeq Analysis

The Kallisto/Sleuth differential expression pipeline analysis was performed for each of the 16 samples. Kallisto was run for single-end read quantification, using the parameters: kmer size=31, fragment length=280, and sd=25. For each of the 16 samples, kallisto quantified transcript abundance with 10 bootstraps. Normalized transcript abundances were further passed into sleuth, which were then aggregated to gene level.

Oil Red O Assay

MEFs differentiated to day 6 into adipocytes in a 24 well plate are washed twice with PBS, then fixed in 4% paraformaldehyde for 10 minutes. The cells are then washed twice with PBS and once with MilliQ water before being then incubated for 1 minute in 60% isopropanol. Then, the oil red working solution is placed on the cells for 8 minutes. The working solution is prepared from an Oil Red O stock solution consisting of 0.5 g Oil Red O in 100 mL isopropanol which has been heated to 56° C. until the Oil Red O has dissolved. The working solution is prepared by taking 30 mL of stock solution and adding to 20 mL distilled water. The mixture must stand for at least 10 minutes then be filtered before use. After the 8-minute incubation, cells are incubated in 50% isopropanol for 1 minute, followed by another 1 minute incubation in 10% isopropanol, then MilliQ water, followed by tap water. After each of these 1-minute incubations, the fixed, stained cells are placed in MQ water and imaged. The water is removed, and the wells are allowed to dry. The stain can then be eluted in 200 μL 100% isopropanol over a 10 minuted incubation period. The eluted stain is then placed into a 96 well plate, and absorbance is measured at 500 nm.

MTT Assay

MEFs differentiated to day 6 into adipocytes in a 24 well plate, and on day 6 cells are treated with 50 μL of the Cytoselect MTT assay preformulated reagent, which is added directly to media. The cells are incubated in this mixture for 4 hours as violet precipitates form. The cells are then treated with 500 μL of the supplied detergent solution for 2 hours, and wells are agitated with pipetting to enhance the dissolution of the precipitate. The detergent with dissolved precipitate is then moved to a fresh 24 well plate and absorbance is measured at 570 nm.

Lipoprotein Lipase (LPL) Binding Assay

Bovine LPL generously provided by Gunilla Olivecrona (Department of Biomedical Sciences, Umea University, Umea Sweden)[42]. Enzyme activity was determined using $^3$H radiolabeled substrate as previously described[43]. Molar ratio of biotin to LPL was determined in a HABA displacement assay (Pierce Biotin Quantitation Kit).

LPL binding assays were performed similar to as previously described. Cells were harvested using Accutase cell detachment solution (Millipore) and washed twice with PBS. Cells were incubated for 15 min at 37° C. in serum free media in the absence or presence of 5 mU/ml each of recombinant heparin lyases 1, 11, and 111. Treated and untreated cells were washed twice with PBS, chilled on ice for 20 min and incubated with 50 nM biotinylated LPL in 1% BSA supplemented PBS at 4° C. for 1 hour. Following the incubation, cells were washed twice in ice-cold PBS and incubated with 0.4 μg/mL Phycoerythrin-Cy5 conjugated Streptavidin in 1% BSA supplemented PBS at 4° C. A set of cells was exposed only to Phycoerythrin-Cy5 conjugated Streptavidin and was used as background control. Cells were washed twice with PBS and analyzed by flow cytometry.

VLDL Binding to Adipocytes.

Human VLDL (o<1.006 g/ml) was isolated from plasma by buoyant density ultracentrifugation and quantified by BCA protein assay (Pierce) as described.[30] To label the particles, 1-2 mg of VLDL were combined with 100 μL of 3 mg/mL 1,1'-dioctadecyl-3,3,3',3'-tetramethylindodicarbocyanine perchlorate (DiD; lnvitrogen) in DMSO and then re-isolated by ultracentrifugation. After incubation with VLDL for 30 min at 4° C., cells were rinsed with PBS and lysed by adding 0.1 M NaOH plus 0.1% SDS for 40 min at room temperature.[30] Fluorescence intensity was measured with appropriate excitation and emission filters in a plate reader (TECAN GENios Pro, Switzerland) and normalized to total cell protein.

Glucose and Lactate Quantification

MEFs are differentiated to day 6 into adipocytes in a 24 well plate, and on day six (6) 500 μL of media is collected from each well in an Eppendorf tube and immediately frozen in liquid nitrogen. Once all samples are collected, the frozen samples are thawed on ice and filtered through an Amicon ultra 3000 molecular weight cut-off centrifugal filter at 4° C. Then, the filtrate is analyzed using a YSl 2900, where the sample is loaded into two wells of a 96 well plate, 200 μL media per well. The samples are then analyzed for lactate and glucose concentration.

3[H]-2-Deoxy-Glucose Uptake Assay

Cells are washed twice with PBS and placed into DMEM with 2 mg/mL BSA for two hours. Then, if cells are to be insulin stimulated, they are treated with 200 nM insulin for 30 minutes at 37° C. in freshly prepared transport solution consisting of 137 mM NaCl, 1.2 mM MgSO4, 1.2 mM KH2PO4, 4.7 mM KCl, 2.5 mM CaCl2), and 20 mM HEPES with a pH of 7.3. The insulin solution is then removed and the cells are washed twice with transport solution before radioactive transport solution is added, which consists of 0.25 μCi/well of 3[H]-2-deoxy-glucose and 0.025 mM 2-deoxy-glucose. After a 10-minute incubation in the radioactive transport solution, it is removed and the, the glucose uptake is halted by addition of ice cold PBS. The cold PBS is removed and each well is washed twice with PBS. Then, lysis buffer consisting of 0.1 M NaOH and 0.1% w/v sodium dodecyl sulfate, is added to each well. The radioactive lysate was transferred to a scintillation vial containing 5 mL of Ultima Gold liquid scintillation fluid and analyzed using a liquid Scintillation counter.

Palmitate Tracer Study

MEF cells on day 8 of adipogenesis were incubated for 6 h in 100 uM [U-$^{13}$C16]Palmitate-containing media. The media contained 10% delipidated FBS and 5% (v/v) of a BSA-conjugated [U-$^{13}$C16]Palmitate stock. To make the stock, briefly, 100 mM [U-$^{13}$C16]Palmitic acid was dissolved in ethanol at 50° C. A solution of 4.4% essentially FA-free BSA (Sigma) in PBS was warmed to 37° C. A 50:1 mixture BSA:Palmitate solution was made and incubated at 37° C. for 1-2 hours before aliquoting and freezing in glass tubes. The stock contains a 3:1 FA:BSA ratio. After incubation, cells are lysed on ice and prepared for GC-MS analysis, as previously reported.

[9,10-$^{3}$H(N)]-Palmitate Uptake Assay

Cells are washed twice with PBS and placed into DMEM with 2 mg/mL BSA for two hours. During this time, 14C-palmitic acid is complexed with BSA at a molar ratio of 1:1 for 30 minutes. After the cells have been starved for 2 hours, the cells washed twice with PBS and incubated in radioactive transport solution (see 2-deoxyglucose uptake assay for contents of transport solution) with 1 μCi/well $^{14}$C-palmitic acid:BSA for 10 minutes. After a 10-minute incubation in the radioactive transport solution, it is removed and the glucose uptake is halted by addition of ice cold PBS. The cold PBS is removed and each well is washed twice with PBS. Then, lysis buffer consisting of 0.1 M NaOH and 0.1% w/v sodium dodecyl sulfate, is added to each well. The radioactive lysate was transferred to a scintillation vial containing 5 mL of Ultima Gold liquid scintillation fluid and analyzed using a liquid Scintillation counter.

Plasma Membrane Isolation

Membrane isolation was performed according to previously published procedures. Briefly, Cells from 10-cm dishes were washed with ice-cold PBS, then scraped in 1 mL hypotonic lysis medium (HLM) containing 50 mM HEPES, 50 mM sucrose, 1 mM EDTA, 100 mM NaCl and 1×PlC and were lysed using a Dounce homogenizer (~50 strokes). Lysates were centrifuged at 5000 g, 4° C. for 10 min. The supernatant was centrifuged at 100,000 g, 4° C. for 30 min. The resulting supernatant represented the cytosolic fraction; membrane pellets were resuspended in R1PA buffer with 1×PlC for Western blotting.

Insulin Stimulation

MEFs differentiated to day 6 into adipocytes in a 24 well plate in the presence or absence of exogenous heparin (100 μg/mL), and on day 6 cells are washed with PBS and serum starved for 2 hours in DMEM with 2 mg/mL BSA. After 2 hours, each well is stimulated with insulin at a final concentration of 10 nM, with the insulin delivered directly to the serum free media as a 10 μL aliquot. The plate in then place into an incubator at 37° C. for the indicated amount of time. After stimulation, the entire 24 well plate is placed on ice, and the wells are washed with ice cold PBS twice. Then, 100 μL R1PA buffer with protease inhibitor (PlC) and phosphostop is added to each well. The cell lysate is collected into an eppendorf, placed on ice for 30 minutes, and then centrifuged at 14,000×g at 4° C. for 15 minutes. The supernatant is then transferred to a fresh tube and protein concentration is determined using a BCA assay.

Western Blot Analysis

Cells were lysed using RIPA buffer, and protein was quantified using a BCA assay. Protein was analyzed by SDS-PAGE on 4-12% Bis-Tris gradient gels (NuPage; lnvitrogen) with an equal amount of protein loading. Proteins were visualized after transfer to lmmobilon-FL PVDF membrane (Millipore). Membranes were blocked with Odyssey blocking buffer (L1-COR Biosciences) for 30 min and incubated overnight at 4° C. with respective antibodies. Goat, mouse, and rabbit antibodies were incubated with secondary Odyssey 1R dye antibodies (1:14,000) and visualized and analyzed with an Odyssey 1R imaging system (L1-COR Biosciences).

Determination of Wnt Binding to HS-Mimetics Via ELISA

Wnt5a and Wnt10b proteins (10 nM solution in 1% (w/v) BSA/DPBS) were immobilized on 96-well tissue culture treated plates overnight at 4° C. The plates were washed twice with 0.05% (v/v) Tween-20 in DPBS and blocked with 1% (w/v) BSA/DPBS for 6 hours at room temperature. Biotinylated HS-mimetic glycopolymers GP or heparin were added to the wells at increasing concentrations in 1% (w/v) BSA/DPBS. After 1 hour incubation, the wells were washed three times with 0.05% Tween-20 in DPBS. Streptavidin-HRP (1:1000 in 1% BSA/DPBS) was added for 45 min at ambient temperature. The wells were again washed three times in 0.05% Tween-20 in DPBS, followed by treatment with 100 μL of TMB substrate for 2-5 min before quenching with 100 μL of 2N sulfuric acid. Absorbance (450 nm) was measured using a Molecular Devices SpectraMax plate reader.

Synthesis and Characterization of Glycopolymers

Glycopolymers were prepared as reported in Huang et al. *J. Am. Chem. Soc.* 136: 10565-10568 (2014), which is incorporated by reference as if fully set forth herein. Protected poly(acrylamide) backbone P terminated with DPPE-lipid and a sulfhydryl group (Number Average Molecular Weight (Mn)=41,562 g/mol, Weight Average Molecular Weight (Mw)=53,061 g/mol, DP=160, and Đ=1.28.) was used as the precursor for glycopolymer assembly. HS-mimetic glycopolymers (GPs) were generated from precursor P in a one pot synthesis through sequential chain-end labeling with AF488-maleimide reporter, side chain deprotection, and glycan ligation. The efficiency (%) of polymer chain labeling with AF488 and side-chain modification with glycans for each GP were determined by UV-Vis and $^{1}$H NMR analysis.

MEF Surface Remodeling with Membrane-Targeting HS-Mimetics

MEFs were cultured in 12-well plates until confluent. The cells were washed with DPBS and incubated with 200 μL solution of serum free media (DMEM) with or without the HS-mimetic glycopolymers (GP) at indicated concentrations for 1 hour at 37° C. After this time, the cells were washed with DPBS and dissociated from the plate using 0.25% trypsin. HS-mimetic membrane incorporation was analyzed by flow cytometry on a BD FACS Calibur instrument, with a minimum of 10,000 events collected per condition. Data were analyzed using FlowJo software and samples were gated to a polymer untreated control.

Adipogenic Differentiation of HS Mimetic-Engineered MEFs

Cells were differentiated for 6 days using the standard adipogenic differentiation protocol described above. Each day on Days 0-3, the cells were washed with PBS and incubated with 200 μL solution of DMEM containing GPs at the indicated concentrations added for 1 hour at 37° C. After this time, the media were removed, the cells were washed with PBS, and fresh differentiation media were added. On Day 6, the adipocytes were subjected to the $^{3}$[H]-2-deoxyglucose uptake assay and the spent media were analyzed for glucose and lactate content as described above.

Statistical Analysis

If not otherwise stated results are mean values±SEM of at least three independent experiments or mice or results show one representative experiment out of three. Statistical analysis was done on all available data. Statistical significance was determined using the 2-tailed student's t-test, one-way ANOVA followed by a Bonferroni post hoc test or two-way ANOVA to compare time courses. For statistical analysis GraphPad prism software was used. * ($p<0.05$),  ($p<0.01$), * ($p<0.001$).

3-azido-coumarin-7-sulfonyl fluoride (ACS-F) Synthesis

To a 4 mL vial containing 3-azido-7-hydroxycoumarin (100 mg, 0.49 mmol, 1.0 eq.) and 4-[(Acetylamino)phenyl] imidodisulfuryl difluoride (AISF, 186 mg, 0.58 mmol, 1.2 equiv.) was added anhydrous DMSO (1.6 mL) followed by 1,8-diazabicyclo [5.4.0]undec-7-ene (DBU, 161 μL, 1.08 mmol, 2.2 equiv.) over a period of 60 seconds. The reaction mixture stirred at ambient temperature for 1 h, diluted with ethyl acetate and washed with 0.5 N HCl (2×) and once with brine. Combined organic fraction was dried with anhydrous magnesium sulfate and concentrated under reduced pressure. The crude residue was purified by silica gel flash chromatography (0→40% EtOAc/Hex with elution at ~15% EtOAc/Hex) to afford the product (35 mg, 28% yield) as a crystalline clear solid. $^1$H NMR (500 MHz, CDCl3) δ 7.54 (d, J=8.6 Hz, 1H), 7.37 (d, J=2.3 Hz, 1H), 7.30 (ddd, J=8.6, 2.4, 0.7 Hz, 1H), 7.21 (s, 1H). $^{13}$C NMR (126 MHz, CDCl3) δ 156.47, 151.52, 149.88, 128.93, 127.91, 124.00, 119.78, 118.10, 110.09 ppm. $^{19}$F NMR: (282 MHz, CDCl3) δ 39.0 (s, 1F). Absorbance and fluorescence spectra were obtained by analyzing unreacted and Heparin-conjugated to ACS-F by absorbance scan pedestal analysis on a Nanodrop 2000c or fluorescence excitation and emission scan on a fluorimeter, respectively.

GAG Conjugation to ACS-F

Commercial GAGs including heparin (20 mg, Iduron, Macclesfield SK10 4TG, UK), TEGA recombinant HS (rHS), or biologically-sourced GAGs were transferred to a PCR tube and dissolved in 90 μL of 1 M urea, 1 M sodium acetate, pH 4.5 buffer. To this solution was added 10 μL of a 1.15 M n-methylaminooxy-propylamine linker[34] (11.5 μmoles). Reducing end conjugation proceeded at 50° C. for 24-48 h. The reaction was quenched with 200 μL of 2 M Tris-HCl, pH 8.1 and GAG-amine was purified by PD-10 column, followed by concentration and removal of excess linker using 3 kDa molecular weight spin filters as per manufacturer's instructions (Amicon, Millipore Sigma, St. Louis, MO). To 400 μL of recovered GAG-amine was added 200 μL of 100 mM sodium phosphate, pH 8.0 and 600 μL DMSO. ACSF (38 mg, 133 μmoles) was dissolved in 400 μL DMSO and transferred to the GAG-amine solution. Sulfonyl fluoride exchange (SuFEx) proceeded at ambient temperature, shaking for 24 h. The reaction was diluted with 900 μL water and similarly purified over PD-10 column with elutions collected in a CoStar clear 96-well plate and analyzed by microplate absorbance at 326 nm to visualize ACS-GAG and excess ACS-F fractions. ACS-GAG fractions were pooled and similarly concentrated by 3 kDa spin filtration, followed by lyophilization.

BCN-BSA Synthesis

To a 1.5 mL microcentrifuge tube (Fisher scientific, Cat. No. 05408129) was added 1 mL of 100 mM sodium phosphate buffer, pH 8.0, 10 mg BSA (VWR, Cat. No. 0332-25G), and 78.1 μL of a 10 mg/mL (1R,8S,9s)-Bicyclo[6.1.0] non-4-yn-9-ylmethyl N-succinimidyl carbonate (BCN, 17 eq.) (Sigma Aldrich, Cat. No. 744867-10MG) and stirred at 4° C. for 16 h. The reaction was dialyzed against MilliQ water in 25 kDa molecular weight cut-off dialysis tubing (Spectra, Cat No. 132126), for 48 hours, replacing water after 24 hours. Lyophilization of the dialyzed product affords 11 mg of the product (quantitative yield). MALDI-TOF MS analysis indicates the modified BSA protein has a molecular weight of about 69,689 daltons compared a starting mass of 66,808 daltons for unmodified BSA. Each additional BCN adds 177.3 daltons, a difference of 3,259 daltons indicates approximately 16 BCN/BSA.

ACS-GAG Conjugation to BCN-BSA

To the wells of a black, clear-bottom CoStar 96-well plate were added either 200 μL PBS, 50 μL of 600 μM ACS-F (30 nmoles), 50 μL of 600 μM ACS-GAG (30 nmoles), 100 μL BCN-BSA (1 mg/mL in water, 1.5 nmoles BSA and 24 nmoles BCN), 50 μL ACS-F+100 μL BCN-BSA, or 50 μL ACS-GAG+100 μL BCN-BSA. Each well was brought up to a final volume of 200 μL with PBS. Using a microplate spectrophotometer, kinetic fluorescence readings were collected with Ex. 393 nm/Em. 477 nm at various time points initially after addition of all reagents to 24-48 h. Post-incubation at ambient temperature for 26 h, wells containing neoPG (GAG-BSA) or TCS-BSA (triazole) were filtered (5×500 μL water) through a 30 kDa molecular weight spin filter to remove unreacted GAG and ACS-F. The recovered 40 μL of neoPG or TCS-BSA was transferred into separate PCR tubes and water was added to a final concentration of 200 ug/mL BSA assuming 96% BSA recovery based on manufacturers data sheet and confirmed by BCA assay. The TCS-BSA and neoPG samples were further diluted for adsorption onto 96-well plates for binding assays.

Figure 1B:
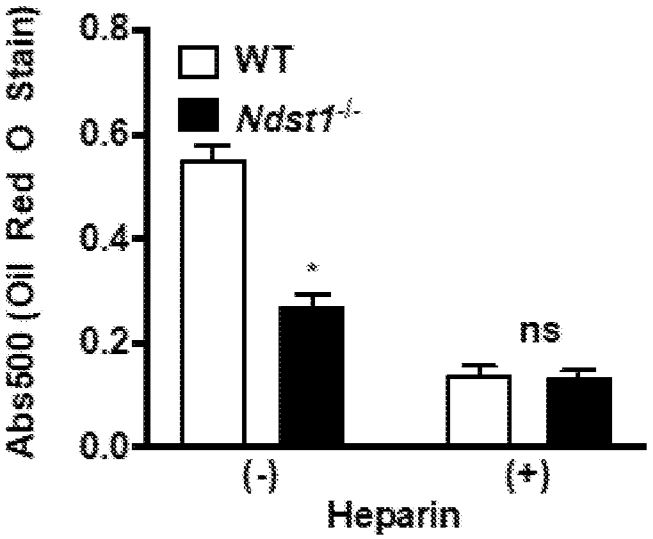
FIG. 1B is a quantified Oil red stain performed by elution of stain (Two-way ANOVA, n=3).
Figure 1C:
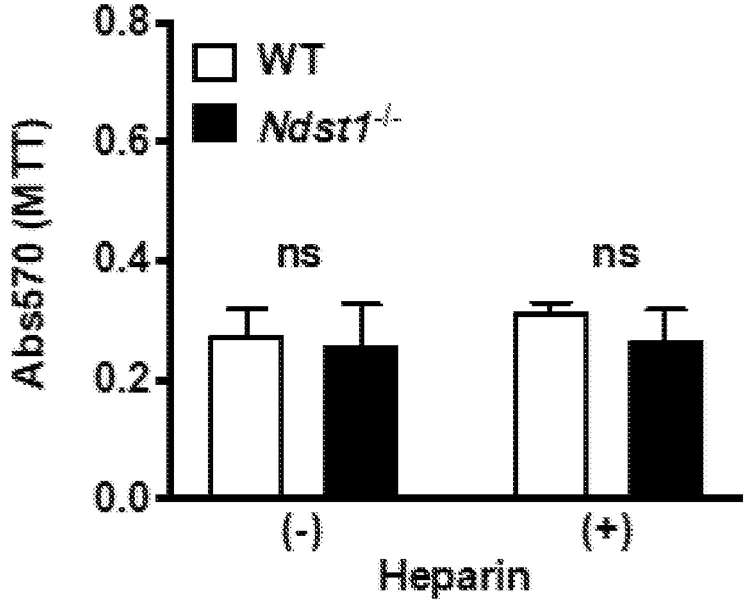
FIG. 1C shows an MTT assay of WT and Ndst1$^{-/-}$ adipocytes treated with or without heparin (100 μg/ml). (n=3). The MTT assay measured cellular metabolic activity as an indicator of cell viability, proliferation and cytotoxicity. The MTT assay is a colorimetric assay based on the reduction of a yellow tetrazolium salt (3-(4,5-dimethylthiazol-2-yl)-2,5-diphenyltetrazolium bromide or MTT) to purple formazan crystals by metabolically active cells.
Figure 1D:
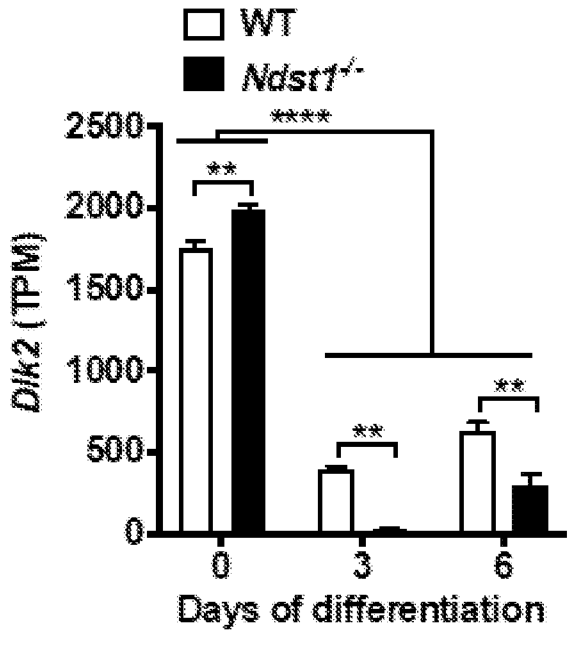
FIGS. 1D-K shows RNAseq quantification of adipogenesis markers in transcripts per million (TPM) relative to day 0 expression levels of WT and $Ndst1^{-/-}$ MEFs undergoing adipogenesis (Two-way ANOVA, n=2). Individually.
Figure 1E:
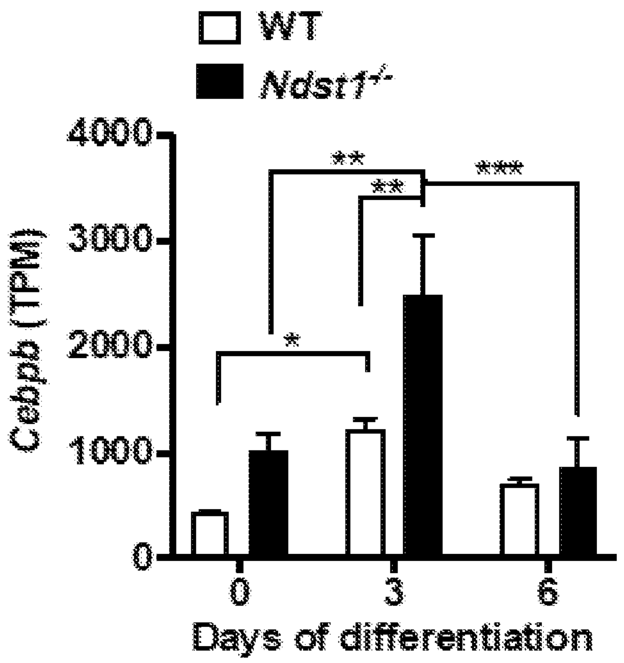
Figure 1F:
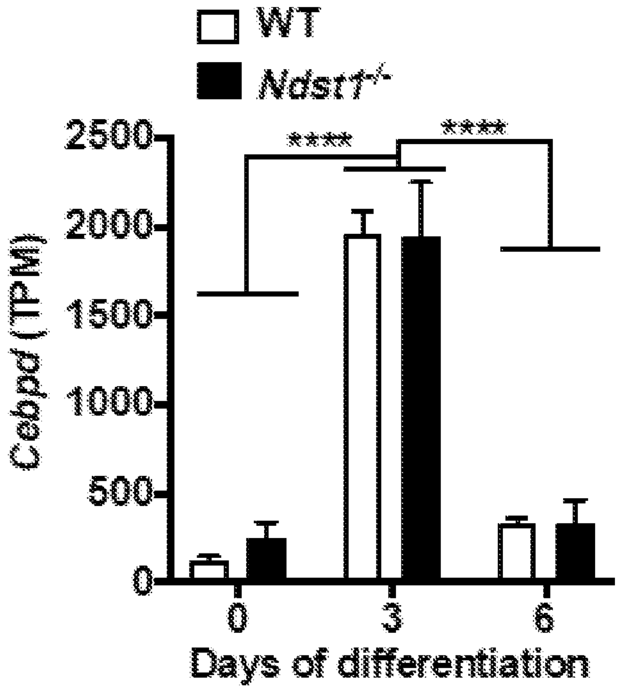
Figure 1G:
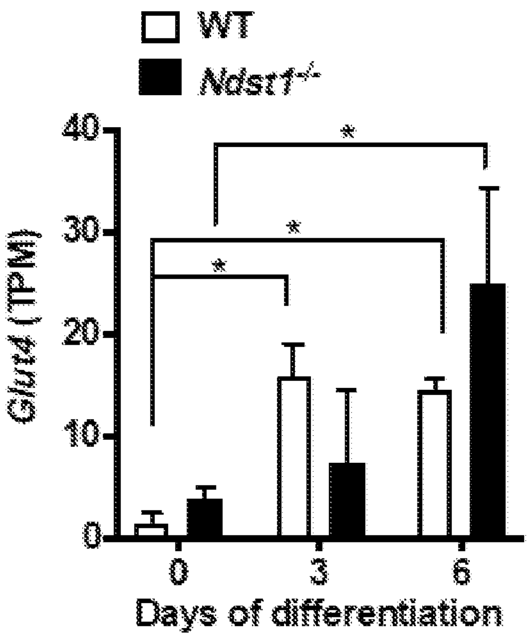
Figure 1H:
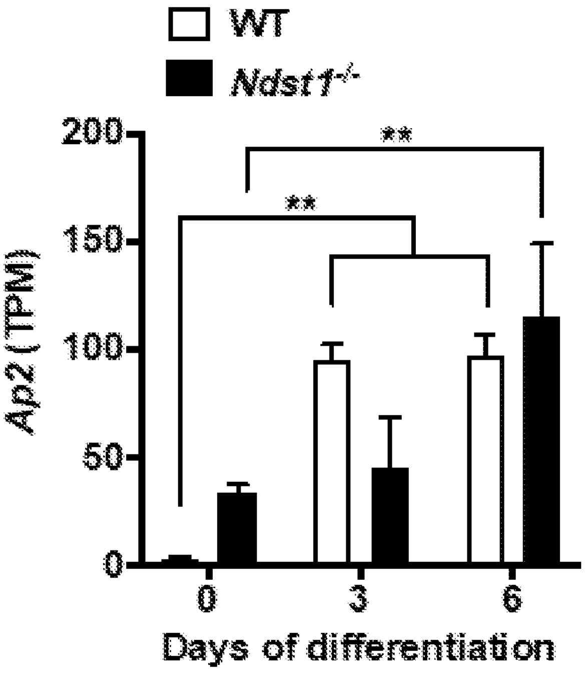
Figure 1I:
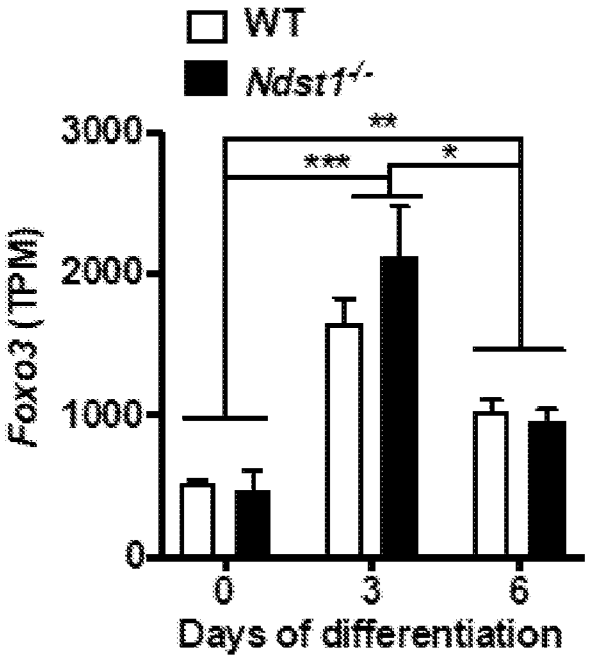
Figure 1J:
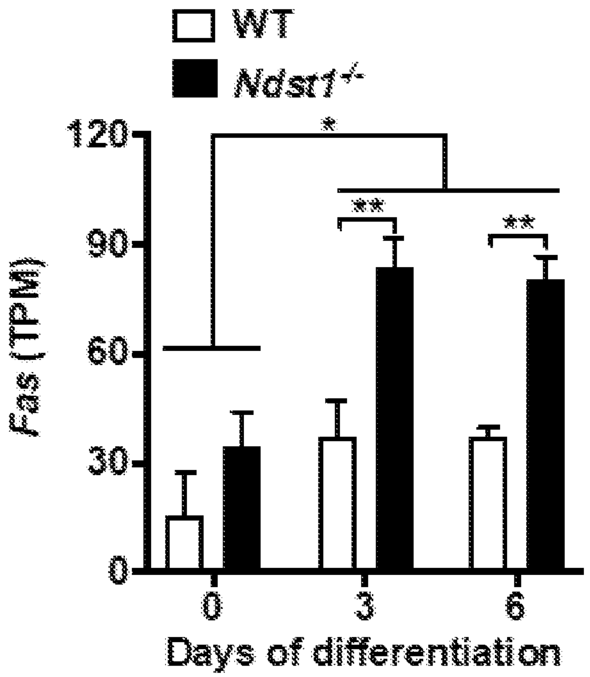
Figure 1K:
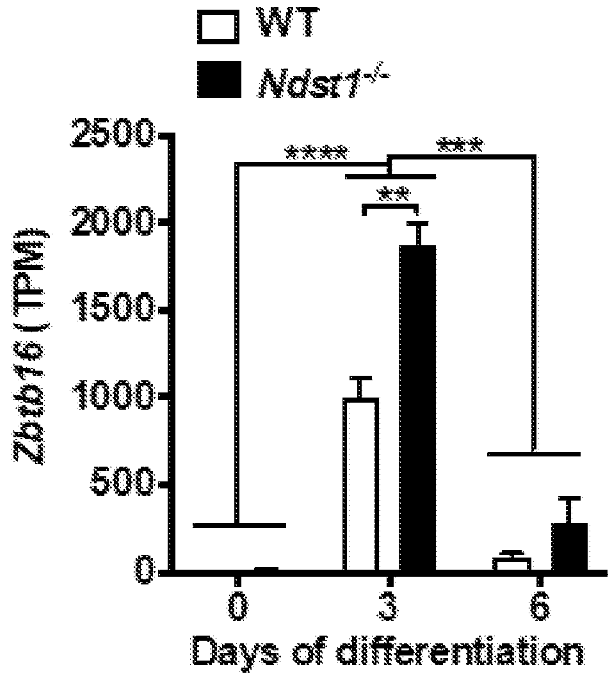
Figure 1L:
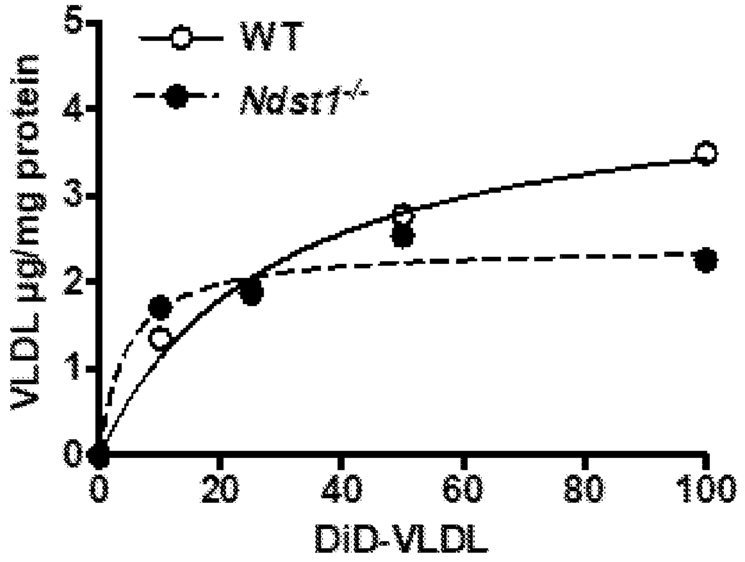
Figure 1M:
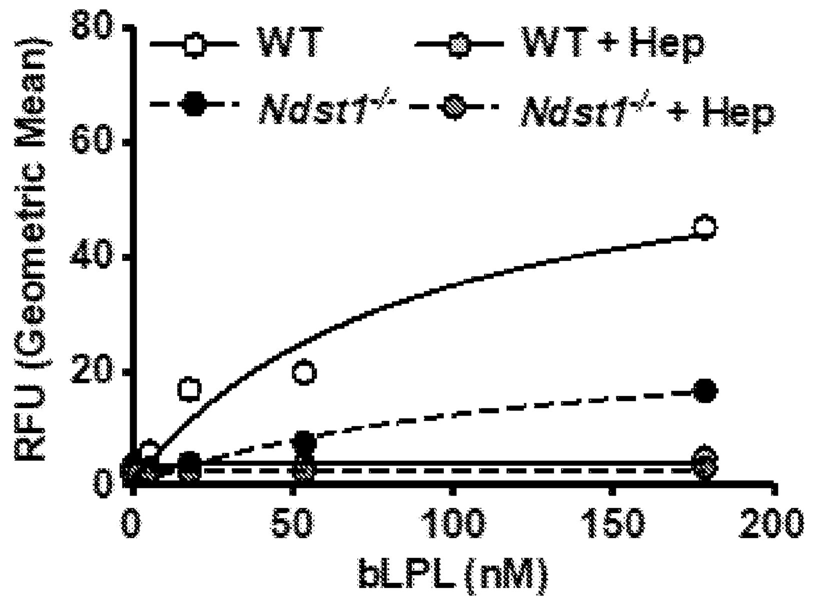
Figure 1N:
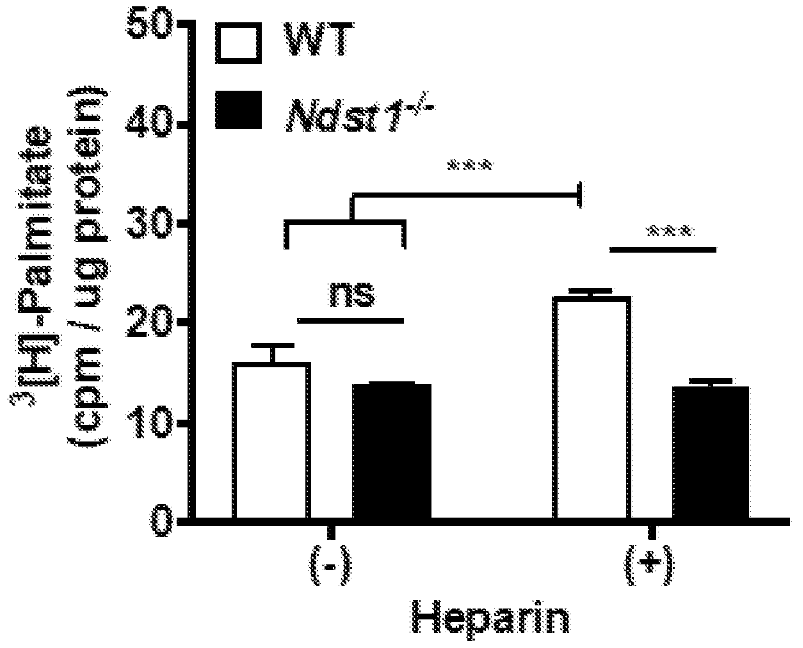

Example 2: Heparan Sulfate Deficiency Prevents Lipid Accumulation in Mature Adipocytes To define the impact of HS during adipogenic differentiation on establishing the metabolic setpoint of adipocytes, immortalized mouse embryonic fibroblasts (MEFs) with defective HS biosynthesis were utilized. As a model, MEFs lacking the HS biosynthetic enzyme, N-deacetylase-N-sulfotransferase 1 (Ndst1), were utilized which generates sulfate domains that modulate interaction of HS with its binding proteins.[27] Significantly diminished lipid storage was observed in adipocytes after differentiation of these Ndst1-deficient (Ndst1$^{-/-}$) MEFs (FIG. 1A-B). The lack of lipid accumulation was not the result of altered growth rate (FIG. 1C), nor a consequence of defective adipogenesis (FIG. 1D-K). Comparison of several adipogenic markers in Ndst1$^{-/-}$ MEFs to WT cells indicated normal adipogenesis regardless of defects in HS biosynthesis. A similar phenotype was generated in wildtype MEFs during adipogenesis upon treatment with high dose of heparin (100 μg/ml), which is a highly sulfated form of HS that serves as a competitive inhibitor for cell surface HS (FIG. 1A-C). Previous studies in pre-adipocytes indicated that exogenous heparin treatment and Ndst1 inactivation reduced lipid accumulation by interfering with HS-mediated endocytosis of triglyceride-rich lipoproteins, including very-low density lipoprotein (VLDL). In contrast, Ndst1 inactivation in MEF-derived adipocytes had no effect on VLDL binding and uptake (FIG. 1L). Exogenous heparin or Ndst1 inactivation resulted in reduced binding of lipoprotein lipase (LPL), an HS-binding protein responsible for the release of free fatty acids (FFAs) from VLDL (FIG. 1M). This protein is not expressed in MEFs according to RNAseq analysis and thus not likely contributes to lipid accumulation. Furthermore, genetic or chemical inhibition of HS did not negatively affect FFA uptake (FIG. 1N), suggesting collectively that altered lipid accumulation upon HS inactivation was independent of lipid uptake.

Example 3: HS Inactivation in Pre-Adipocytes Alters Insulin-Independent Glucose Uptake after Differentiation (the Loss of Cell Surface Heparan Sulfate Interactions During Adipogenesis Reduces Glucose Uptake)

Insulin-stimulated glucose clearance is one of the primary functions of adipocytes. The potential discrepancy between reduced lipid storage and unaltered lipid uptake can be a consequence of altered cellular glucose metabolism. The impact of HS function in MEFs on glucose uptake was examined in mature adipocytes. Approximately an 84% reduction of glucose uptake was observed in Ndst1− deficient adipocytes, which was paralleled by a 45% reduction in WT cells treated with exogenous heparin. Treatment of Ndst1$^{-/-}$ with exogenous heparin did not have an additive effect on glucose uptake. Ndst1$^{-/-}$ adipocytes have a significantly reduced glucose uptake potential relative to WT adipocytes (Two-way ANOVA, n=2). Further, soluble heparin treatment (100 μg/ml) of WT adipocytes reduces glucose uptake potential relative to untreated WT adipocytes (Two-way ANOVA, n=2).

A similarly impaired glucose uptake was observed in adipocytes derived from primary murine white adipose tissue pre-adipocytes differentiated in the presence of heparin. Primary adipocytes derived from murine subcutaneous white adipose tissue (sWAT) stromal vascular cells exhibited reduced glucose uptake when co-incubated with heparin during adipogenesis (Two-way ANOVA, n=2). Surprisingly, the same differentials in glucose uptake between WT and HS-inhibited cells were maintained after insulin stimulation (−84% and −44% respectively). This observation suggests that HS alters glucose uptake without altering insulin sensitivity. This was supported by similar levels of AKT phosphorylation in WT and HS-inactivated cells upon stimulation with insulin. Western Blot analysis using anti-AKT antibodies showed phosphorylated AKT and unphosphorylated AKT. The Western Blot shows that stimulation of mature adipocytes (day 6) with insulin (20 nM) leads to equal signaling transduction via AKT phosphorylation regardless of HSPG interaction modulation (n=3). The observed diminished glucose uptake could be the result of reduced expression of cell surface glucose transporters, i.e., GLUT1 and GLUT4. However, western blot analysis of isolated plasma membrane fractions indicated unaltered levels of GLUT4 and GLUT1 in response to HS inactivation. Western Blot analysis using anti-LRP1 and anti-GLUT4 antibodies showed similar levels of expression of Glut4 at the cell surface of WT and HSPG inhibited adipocytes (n=3). These observations collectively indicate a link between cell surface HS levels and changes in glucose uptake in adipocytes, which is independent of glucose transporter expression and insulin activity.

Example 4: HS Inactivation Induces a Switch from Glycolysis to Oxidative Metabolism (Heparan Sulfate Deficiency During Adipogenesis Promotes Fatty Acid Oxidation)

A decrease in glucose uptake without changes in glucose transporter expression in HS− inactivated adipocytes can stem from reduced cellular glucose utilization. The attenuated demand for cellular glucose could be the result of a switch from glycolysis to fatty acid dependent oxidative metabolism. Such a metabolic switch can occur based on the observed reduction in lipid storage and lactate production in HS− inactivated adipocytes. In culture, WT adipocytes produce a greater amount of lactate than Ndst1$^{-/-}$ adipocytes or adipocytes treated with heparin (100 μg/ml) during differentiation, as observed by discoloration of the phenol red indicator. This decreased lactate production was also mirrored by high glucose levels remaining in the culture medium when glucose and lactate were measured in cell media using a YSI analyzer on spent media collected on the final day (day 6) of adipogenesis. Typically, reliance on oxidative metabolism will drive breakdown of intracellular lipids that can be compensated for by increased fatty acid uptake from external sources. Accordingly, a significant reduction in intracellular palmitate levels and increased influx of isotopically labeled [U-$^{13}$C16] palmitate in HS-inactivated cells was observed. The abundance of palmitate relative to control WT cells from saponified lipids was measured using mass spectroscopy, which indicated that total intracellular palmitate is higher in WT control cells (Two-way ANOVA, n=3). Heparan sulfate inhibition increased palmitate uptake from external sources compared to control WT adipocytes to compensate for increase fatty acid utilization (Two-way ANOVA, n=3). Under oxidative metabolism, palmitate is converted into citrate via the citric acid (TCA) cycle. In agreement with enhanced oxidative metabolism in HS-inactivated cells, a significant increase in isotopically labeled citrate production was observed. Assays of [U-40$^{13}$C16] palmitate metabolism indicated that palmitate was increasingly converted to citrate in heparan sulfate-inhibited adipocytes compared to control WT controls (Two-way ANOVA, n=3). Collectively, these observations support a switch in the metabolic program of adipocytes induced by HS.

Example 5: HS Defines Metabolic Activity of Adipocytes During Early Adipogenesis (Heparan Sulfate Modulates Adipocyte Glucose Clearance Capacity Early During Adipogenesis)

To determine if HS defines the metabolic switch during or after adipogenesis, mature WT and Ndst1$^{-/-}$ adipocytes were subjected to a $^{3}$[H]2-deoxyglucose challenge in the presence of soluble heparin or after cell surface HS removal with heparin lyases. Adipocytes simultaneously treated with heparin (100 μg/ml) during 3[H]-2-deoxy-glucose administration exhibit unaltered glucose uptake (n=3) and independent of cell surface heparan sulfate presentation (n=3). Treatment of adipocytes with heparin lyases 1-111 (30 minutes) prior to 3[H]-2-deoxy-glucose uptake does not alter glucose uptake (n=3). Neither method of acute HS inhibition resulted in altered glucose uptake, suggesting a role for HS during adipogenesis. Further support comes from lack of an effect of HS inhibition on glucose uptake in undifferentiated pre-adipocytes (MEF) or in terminally differentiated cells of non-adipogenic origin (Hep3B). Undifferentiated Ndst1$^{-/-}$ MEFs and Ndst1$^{-/-}$ Hep3B (human hepatoma) cells have no significant difference in their $^{3}$[H]-2-deoxy-glucose uptake capacity (n=2). To define the time window during adipogenesis when HS exerts its effect, heparin was added or removed at different timepoints during differentiation and clearance of $^{3}$[H]-2-deoxy-glucose was measured. All conditions except untreated (ctrl.) cells were initially conditioned with heparin (100 μg/ml) in the media. On the indicated days (day (D) 1 up to D6) heparin was removed from media to allow heparin-free differentiation conditions from that day onward. Glucose uptake potential was assessed at day 6 for all conditions. Initial heparin treatment significantly reduced glucose uptake if cells were treated up to day 3 and beyond (Two-way ANOVA, n=3). In another assay, the MEFs began culture with no heparin in the media. Glucose uptake potential was assessed at day 6 for all conditions. Addition of heparin after day 4 of differentiation can no longer impact glucose uptake in mature adipocytes (Two-way ANOVA, n=3). Treatment with heparin for the first three days of differentiation was required to significantly reduce glucose uptake in mature adipocytes. The data point to the role for HS in defining the glucose uptake capacity early in the adipogenic program, focusing a putative mechanism in this three-day differentiation window.

Example 6: The HS-Wnt Signaling Axis Defines the Metabolic Program in Adipocytes HS can regulate cellular differentiation by influencing a number of signaling pathways including the FGF, SHH, TGF-r., VEGF and Wnt superfamilies of signaling proteins. To identify HS-dependent signaling pathways pertinent to metabolic programming in adipocytes, comparative transcriptomic analysis of genetically ($Ndst1^{-/-}$) and chemically (WT+heparin) HS-inhibited MEFs was performed at early (day 3) and late (day 6) stages of adipogenesis. Overall, both genetic and chemical inactivation of HS resulted in a significant change in gene expression compared to WT controls. Not surprisingly, the genetic Ndst1 deletion had a more profound overall effect on the transcriptome compared to the heparin treated MEFs. Nonetheless, both conditions resulted in a shared set of transcripts that were significantly altered compared to WT controls. Metascape analysis of the overlapping sets of genes indicated no major differences in typical adipogenic pathways. A closer examination of enriched transcripts relevant to signaling pathways regulated by HS revealed a characteristic gene signature associated with Wnt signaling. The genes most upregulated by HS inhibition in the early stage of adipogenesis are Wnt readout-effector genes Plpp3, Gli3, Grk5 and Rnf213, indicating strong activation of the Wnt pathway. In agreement with increased Wnt signaling, the genes Sox2, Lgr6 and Klf5 were downregulated in HS inhibited cells compared to WT controls. These observations are consistent with the known role for canonical Wnt signaling in regulating adipocyte metabolism during adipogenesis. However, how HS influences Wnt activity in this particular process is unclear and often context dependent. The data suggest that the functional role of HS is to attenuate Wnt activity during adipogenesis.

Differentiation experiments in WT and $Ndst1^{-/-}$ MEFs were performed in the presence or absence of small molecule inhibitors of Wnt and showed that heparan sulfate modulation of Wnt signaling during adipogenesis promotes glucose clearance in mature adipocytes. The canonical Wnt signaling inhibitors Niclosamide and XAV-939 were used, as well as Wnt-$C_{59}$, which additionally inhibits the non-canonical arm of the signaling pathway. Niclosamide treatment during the first 3 days of adipogenesis was unable to significantly enhance glucose clearance in differentiated WT adipocytes (n=2-3). Niclosamide treatment during the first 3 days of adipogenesis was able to enhance glucose clearance in $Ndst1^{-/-}$ adipocytes at 12.5 nM (One-way ANOVA, n=2-3). Treatment during the first 3 days of adipogenesis of wild type adipocytes with Wnt inhibitor, XAV-939, enhanced glucose clearance in differentiated adipocytes (One-way ANOVA, n=3). Treatment during the first 3 days of adipogenesis of $Ndst1^{-/-}$ adipocytes with Wnt inhibitor, XAV-939, enhanced glucose clearance in differentiated adipocytes (One-way ANOVA, n=3). WT cells differentiated in the presence of Wnt-C59 had no effect on cellular glucose clearance (10 nM was toxic to WT adipocytes). Treatment of $Ndst1^{-/-}$ cells with Wnt-C59 enhanced glucose clearance capacity in differentiated $Ndst1^{-/-}$ adipocytes (One-way ANOVA, n=2-3). All three Wnt inhibitors reversed the effect of Ndst1 deletion on glucose uptake in adipocytes and showed a modest effect in WT cells. These experiments confirm that attenuation of Wnt signaling during early stages of adipogenesis results in enhanced glucose uptake in adipocytes after differentiation.

Figure 2A:
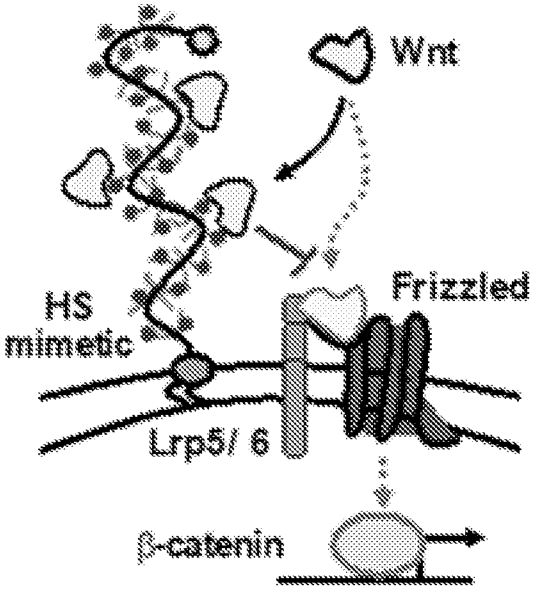
FIGS. 2A-F illustrate that membrane-incorporation of an HS mimetic during adipogenesis rescues the impaired glucose uptake in HS-deficient adipocytes.

Example 7: Chemical Remodeling of the Preadipocyte Glycocalyx Enhances Glucose Uptake after Differentiation The role of cell surface HS in inhibiting Wnt activity is shown, presumably by sequestering the ligand away from its receptor Frizzled (FZD) (FIG. 2*a*). Targeting the Wnt signaling pathway has been suggested previously as a therapeutic opportunity for increasing glucose uptake capacity in adipose tissues. However, only marginal benefits were observed (up to 23% increase in glucose uptake) in WT cells in the presence of chemical Wnt signaling inhibitors at the maximum tolerated dosage.

Figure 2B:
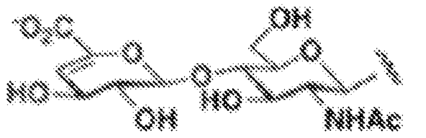
Figure 2B:
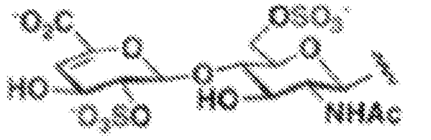
Figure 2B:
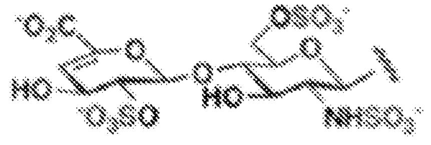
Figure 2C:
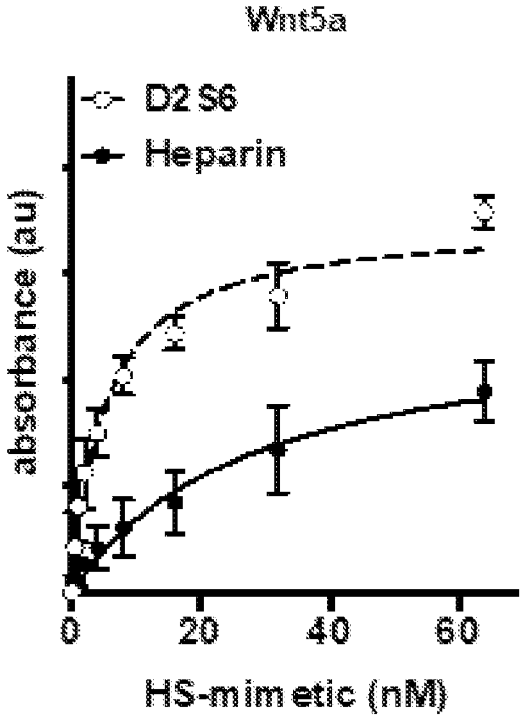
Figure 2D:
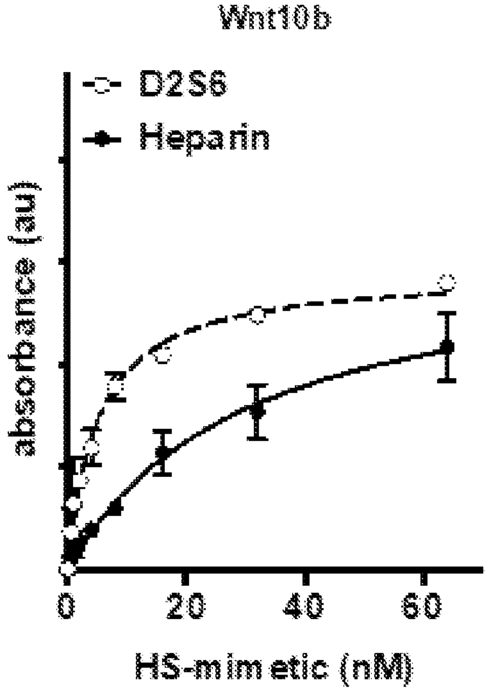
Figure 2E:
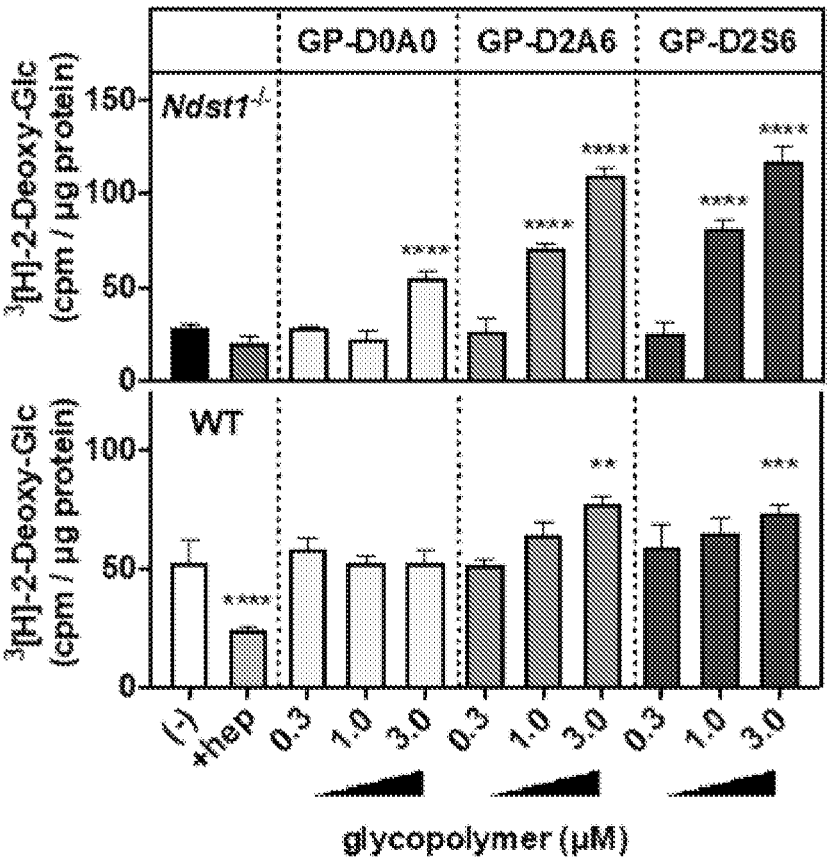
Figure 2F:
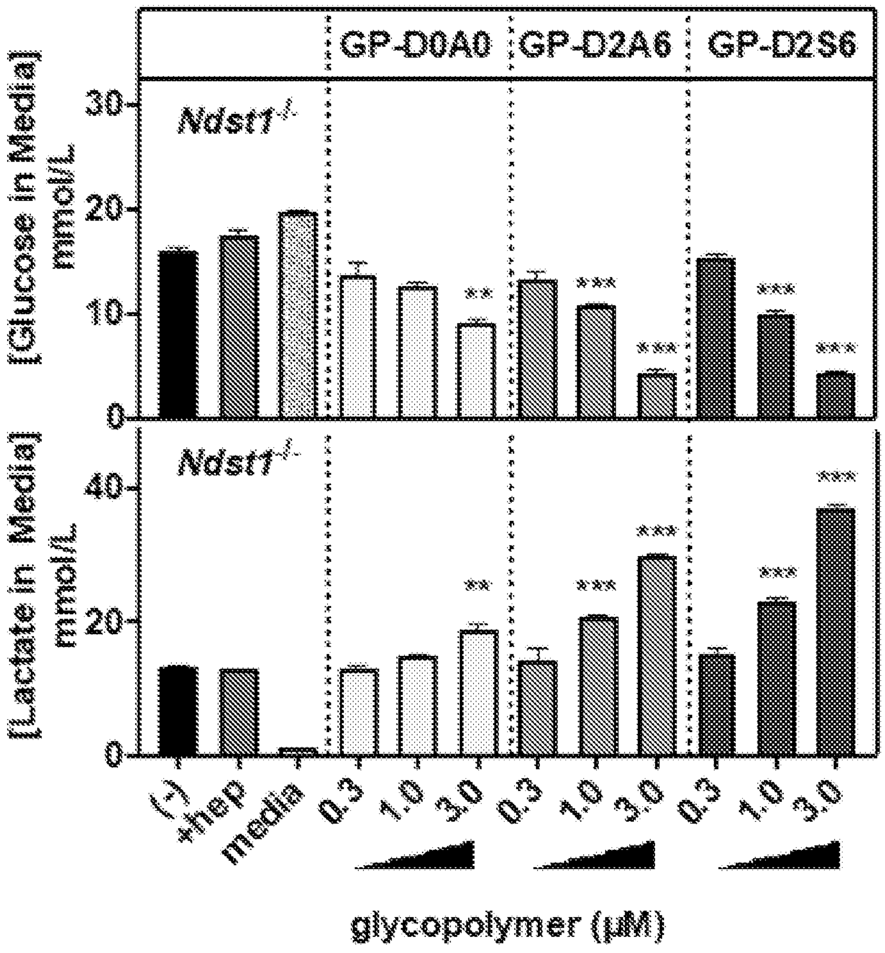

An alternative strategy was to augment the natural capacity of the pre-adipocyte glycocalyx to inhibit Wnt signaling to enhance glucose clearance. Cell surfaces of WT and $Ndst1^{-/-}$ MEFs were engineered to present synthetic mimetics of HS. The HS mimetics comprise a synthetic linear polymer backbone decorated with disaccharide motifs representing the basic structural units of HS (FIG. 2*a*). The disaccharide side-chains were differentially sulfated to provide a range of binding avidity for the Wnt ligands. The HS mimetics carrying the most sulfated disaccharide (D2S6) showed Wnt5b and Wnt10a binding characteristics comparable to heparin (FIG. 2*b*). Additionally, the HS mimetics were endowed with a hydrophobic lipid (DPPE) anchor, for insertion into the cell membranes, and a flurophore (AF488) for quantification. Incubation of pre-adipocytes with the HS mimetics for 1 hour at 37° C. resulted in efficient and dose-dependent cell membrane incorporation. Higher incorporation levels for sulfated HS mimetics in $Ndst1^{-/-}$ MEFs were observed compared to WT controls which can be due to the reduced overall negative charge of HS in the glycocalyx of $Ndst1^{-/-}$ MEFs. The remodeled pre-adipocytes were subjected to differentiation with the polymer being re-introduced once a day over the previously identified HS activity window (Day 0-3). On day 6 of differentiation the adipocytes were assayed for glucose uptake and lactate production (FIG. 2C-D). The sulfated Wnt-binding HS mimetics were able to restore the reduce basal glucose clearance associated with $Ndst1^{-/-}$ inactivation. The membrane targeting of the HS-mimetics is critical for their activity as supplementation with soluble heparin had no effect (FIG. 2C-D). Similarly, sulfation of the disaccharide is important for activity, as the non-sulfate control HS-mimetic D0A0 showing only a limited ability to improve glucose uptake. Importantly, unlike treatment with small molecule Wnt inhibitors, cell surface engineering with HS mimetics carrying the sulfated D2A6 and D2S6 disaccharides significantly improved basal glucose uptake capacity in WT adipocytes by 39% and 47%, respectively (FIG. 2C). This suggests that engineering the glycocalyx of pre-adipocytes to tune Wnt signaling sensitivity may provide a new effective approach for controlling the metabolic status of adipocytes favoring glucose clearance and utilization.

Example 8: Development of Aptamers

Utilizing whole-cell systematic evolution of ligands by exponential enrichment (cell-SELEX), aptamers that selectively bind a cell surface pluripotency marker, alkaline phosphatase (Alpl), was identified for targeting pluripotent cells. The aptamer 19S binds selectively to pluripotent stem cells expressing Alpl and can be used as an enrichment tool in mixed cell populations. Aptamer 19S targeting Alpl has a nucleic acid sequence of SEQ ID NO. 1:

```
AGGTCAGATGAGGAGGGGGACTTAG

GACTGGGTTTATGACCTATGCGTG
```

Figure 3:
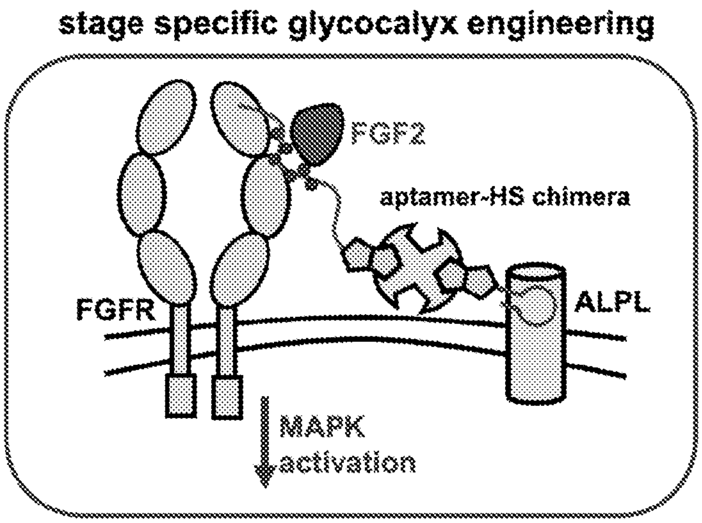
FIG. 3 is a schematic illustrating an aptamer-HS chimera containing a bioactive HS glycodomain linked to an Alpl targeting aptamer via a protein core. The aptamer-HA chimera can activate MAPK activity by facilitating FGF2/FGFR interactions.

Aptamer 19S was connected to heparin (HS) through a streptavidin-biotin interaction to form a HS-aptamer chimera. HS-aptamer chimeras were constructed whereby a fluorescently labeled streptavidin core is non-covalently bound to an HS glycodomain and Alpl target DNA aptamer for cell stage specific binding activity (FIG. 3).

HS-Aptamer Chimera Design

To maximize the potential of our HS-aptamer chimeras to influence neuroectodermal differentiation a cell surface target was identified which is expressed during pluripotency, but expression is quickly lost as the cell exits the pluripotent state. As such, several mouse embryonic stem cell pluripotency markers were identified including Oct4, SSEA-1, and Alpl. SSEA-1 and Alpl were further evaluated as these markers are expressed on the cell surface and ultimately Alpl was selected owing to both the relatively low background expression in other cell types and because a single-stranded DNA aptamer (aptamer 19S) had previously been identified to bind selectively to pluripotent stem cells. See Hou, Z.; Meyer, S.; Propson, N. E.; Nie, J.; Jiang, P.; Stewart, R.; Thomson, J. A. Characterization and target identification of a DNA aptamer that labels pluripotent stem cells. *Cell Res.* 2015, 25(3), 390-393. DOI: 10.1038/cr.2015.7. Heparin was chosen as the bioactive component of the chimera as it could be obtained commercially and could demonstrate efficacy of the approach prior to the use of either tissue derived HS or selectively desulfated HS structures. Because direct bioconjugation of the aptamer and heparin glycodomain proved extremely challenging owing to the size and large negative charge of each component, the chimera was linked via a protein core. The display of heparin from a protein core would physically separate the two negatively charged domains, aiding in their bioconjugation.

Figure 4A:
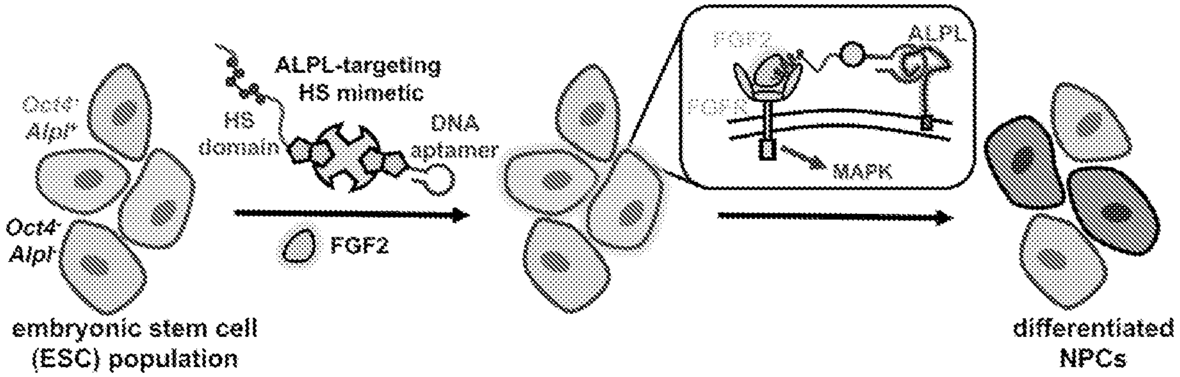
FIGS. 4A-C show glycocalyx engineering of embryonic stem cells (ESC).

The strong binding constant of streptavidin-biotin interactions presented an appealing alternative to covalent bioconjugation owing to the rapid, modular assembly of non-covalent chimera structures. By modifying the aptamer and heparin with biotin, conjugates could be quickly generated with control over composition. Fluorescent labeling of the streptavidin protein core could also be used to introduce an optical probe for visualization of the materials on the cell surface. HS-chimeras assembled in 1:1:1 stoichiometric ratio would simultaneously anchor to the surface of pluripotent Alpl and Oct4 expressing cells (FIG. 4A) Upon binding to the cell surface the materials would be primed to engage FGF2/FGFR complexes and promote MAPK activity, ultimately promoting neural differentiation of the cells toward the neural precursor state, which is assessed by expression of a neuroectodermal marker, Sox1.

Assembly of Heparin Aptamer Chimeras

Figure 5A:
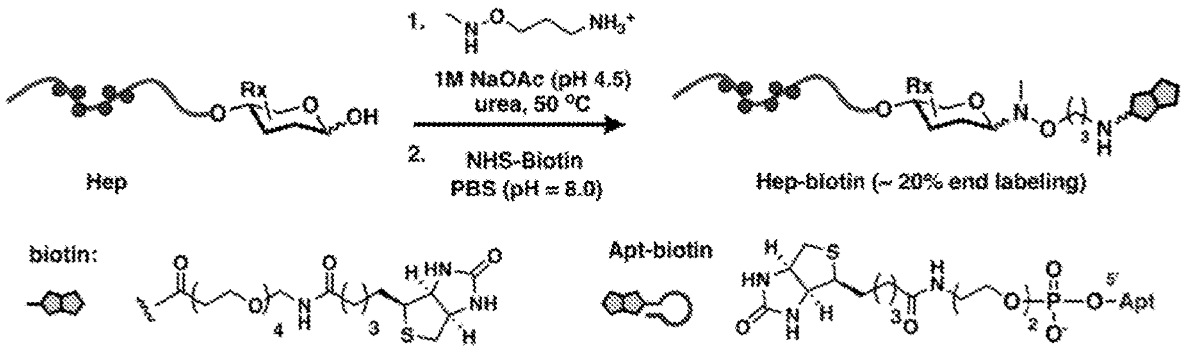
FIGS. 5A-B illustrate the synthesis of the aptamer HS glycoconjugates.

To generate the heparin-aptamer (Hep-aptamer) chimeras, the heparin was first modified at the reducing end. A propylamine linker was used bearing an N-methylaminooxy functional handle with reactivity toward the hemiacetal of reducing heparin under acidic conditions (FIG. 5A). After installing an amine, n-hydroxysuccinimide chemistry could be employed to biotinylate the heparin via a short tetraethylene glycol linker. The resulting heparin was characterized by carbazole17 and 4-hydroxyazobenzen-2-carboxylic acid18 (HABA) assays and determined to be approximately 20% end-functionalized. The modest end-functionalization efficiency may be due to the method of heparin isolation yielding a mixture of free reducing and β-eliminated heparin. Because the heparin-streptavidin (Hep-SA) intermediates will require purification, non-biotinylated heparin was removed from the Hep-aptamer chimeras via dialysis and molecular weight cut-off filtration. Aptamer 19S and a control sequence in which the aptamer binding domain is scrambled (Aptamer Scr) were obtained with 5' biotin modification from Integrated DNA Technologies and used as received.

The scrambled DNA aptamer sequence (Scr) has a nucleic acid sequence of SEQ ID NO. 2:

```
AGGTCAGATGGTGGATTCGAAGTGG

GAGATGCGAGTGTACCTATGCGTG
```

The sequences of aptamer 19S and Scr contain identical wing sequences of approximately ten (10) bases and the high GC content of aptamer 19S affords a G-quadruplex binding motif with specificity for Alpl.

Figure 5B:
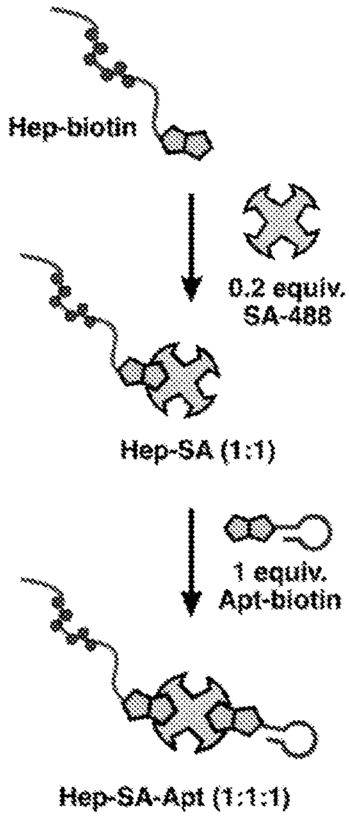

To assemble the Hep-aptamer chimeras, a two-step process was utilized (FIG. 5A) in which excess Streptavidin-AF488 (bearing approximately 5 fluorophores per streptavidin) was first mixed with biotinylated heparin and purified by a combination of dialysis and spin filtration to yield Hep-SA in a 1:1 stoichiometry, as determined by carbazole assay and UV-Vis spectroscopy. The purified Hep-SA is then mixed with exactly 1 equivalent of biotinylated aptamer or scramble sequence to yield Hep-SA-19S or Hep-SA-Scr in 1:1:1 stoichiometry suitable for immediate use (FIG. 5B).

To characterize the assembly of Hep-SA-Aptamer chimeras, agarose gel electrophoresis was performed and samples were visualized via the AF488 optical probe. A mobility shift is observed upon addition of a heparin chain to the streptavidin protein core, pulling the assembly into the gel. A modest shift is observed upon the addition of aptamer, suggesting that electrophoretic mobility afforded by the increase in negative charge is, to some extent, counteracted by the decreasing ability of the material to move through the agarose gel. To corroborate these observations, agarose gels were also stained by SYBR Gold nucleic acid stain, enabling visualization of the DNA aptamer domain. Unsurprisingly, a mobility shift is observed between aptamer and Hep-SA-Aptamer bands, and colocalization of SA and Aptamer 19S signal is observed. Addition of a single equivalent of DNA was optimal as complete consumption of the DNA band was observed, indicating that the material could be used directly in biological assays without further purification.

Stage Specific Glycocalyx Engineering with Hep-SA-Apt Conjugates

Figure 4B:
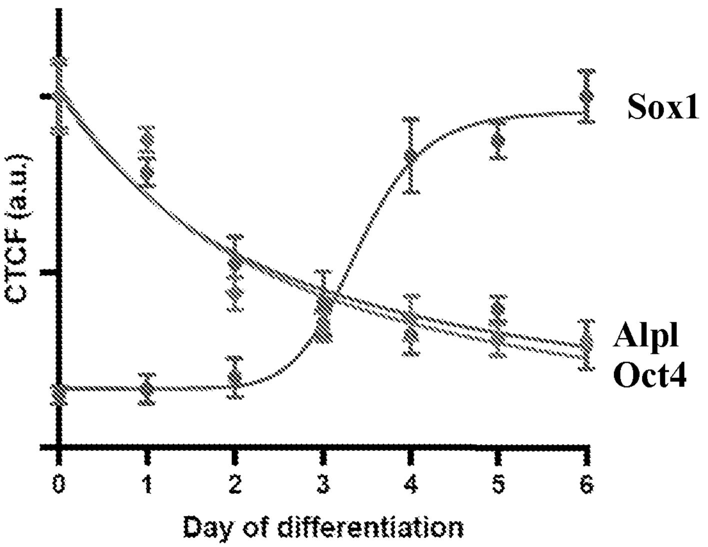
Figure 4C:
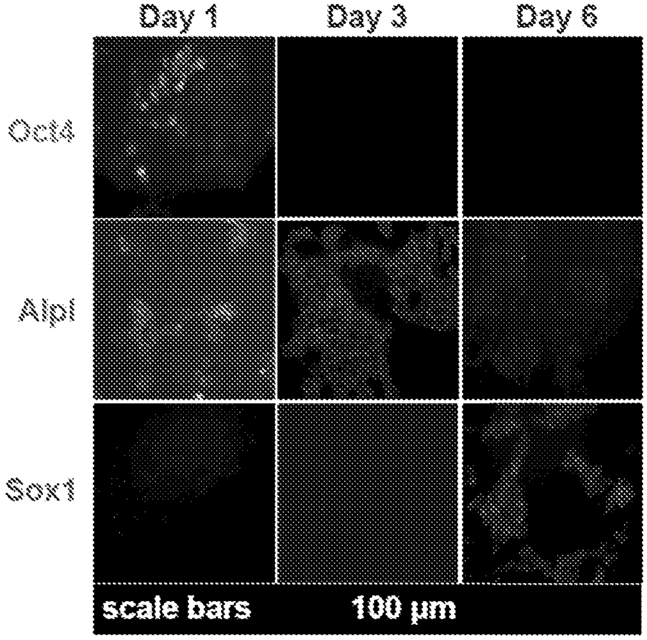
Figure 6A:
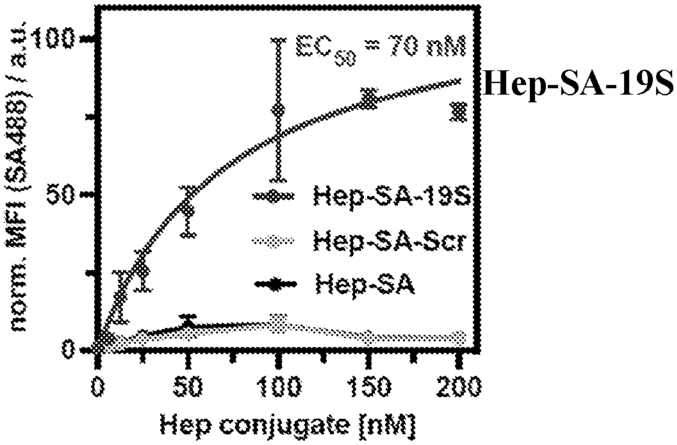
FIGS. 6A-B illustrate binding of Hep-SA-19S to the cell surface of mouse embryonic stem cells, which express Alpl to which the aptamer 19S binds.
Figure 6B:
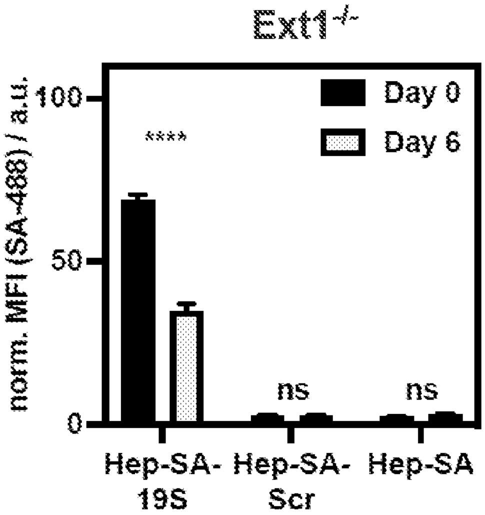
Figure 6C:
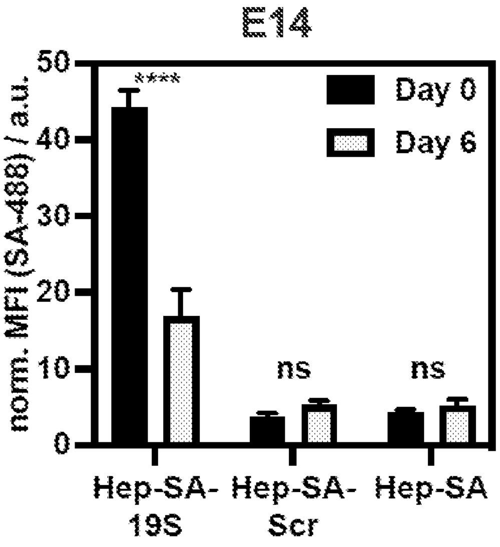
FIG. 6C shows a graph illustrating embryonic stage-specificity of Hep-SA-19S insertion into the glycocalyx of mouse embryonic stem cells that were subjected to neural differentiation protocols until Day 6 in the absence of soluble heparin at a concentration of 5 ug/mL. In both $Ext1^{-/-}$ and E14 (wt) mouse embryonic stem cells, Hep-SA-19S shows significant cell surface binding over control conjugates paired with a significant reduction (p<0.0001) in binding to cells which have undergone six days of neural differentiation. Some binding is retained due to the mixed population of embryonic and differentiated cells following the differentiation protocol.
Figure 7A:
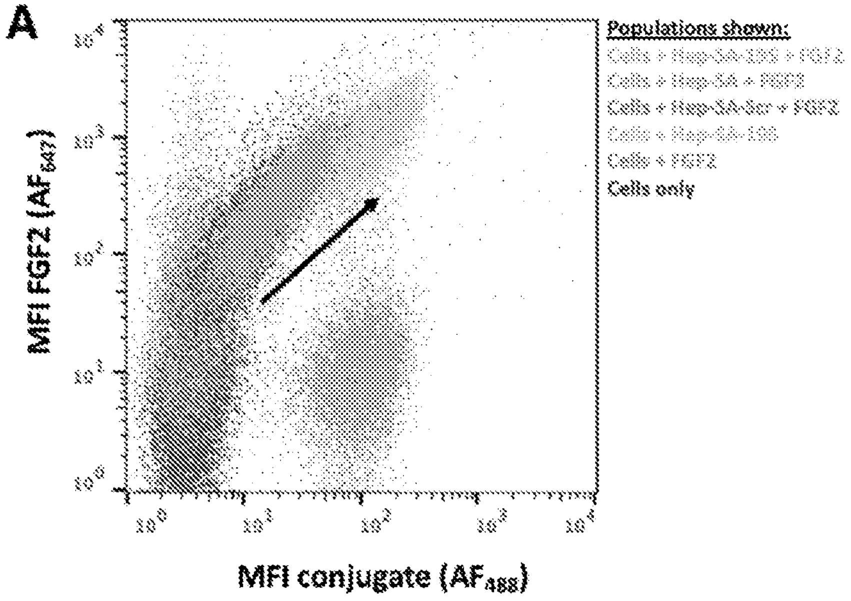
FIGS. 7A-B illustrate the FGF2 binding activity of embryonic stem cells with glycocalyx remodeled with Hep-SA-19S.
Figure 7B:
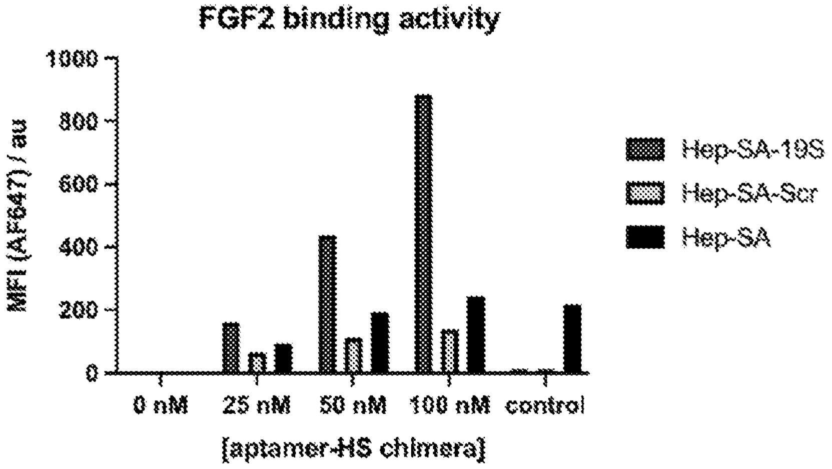

To assess the ability of Hep-SA-Aptamer chimeras to remodel the surface of live cells expressing Alpl, we first evaluated the binding of aptamer biotin alone to the surface of mouse embryonic stem cells ($Ext1^{-/-}$) and differentiated mouse embryonic fibroblasts which do not express Alpl (FIG. 4.S9) and determined the EC50 of aptamer binding to be approximately 107 nM. Expecting that the addition of the Hep-SA domains would result in a similar binding coefficient, chimera binding to the Ext1−/− cell surface was measured at concentrations ranging from 0-200 nM. Hep-SA-Aptamer bound to the cell surface, as determined by flow cytometry after 40 min incubation in suspension, with an observed EC50 of 70 nM while Hep-SA-Scr control and Hep-SA alone did not result in significant cell surface binding (FIG. 6A-C). Notably, the concentration ranges for cell surface remodeling afforded by the aptamer targeting strategy are significantly lower than traditional glycocalyx remodeling via passive insertion of glycomaterials bearing membrane anchors (typically used at concentrations of 0.5-10 uM in vitro). Importantly, Hep-SA-Aptamer showed binding specificity over the control chimeras at concentrations as low as 25 nM.

Example 9: GAG-Protein Conjugates

Glycosaminoglycan (GAG)polysaccharide chains can be end-conjugated to a carrier bovine serum albumin (BSA) protein as a model for the HS mimetic comprising a polymer backbone (e.g. sulfated GAG) and a protein based cell membrane anchoring portion (e.g. an antibody). A strain-promoted alkyne-azide cycloaddition (SPAAC) reaction with a reactive fluorogenic linker can be used to generate the glycoconjugates. The strategy enables efficient coupling with real-time monitoring of GAG conjugation to BSA and quantification of a resulting neo-proteoglycan ("neoPG") composition. This method is suitable for all members of the GAG family, including tissue-derived and bioengineered polysaccharides and the reagents can be immobilized in an ELISA format to analyze GAG-binding protein interactions or used as soluble reagents to evaluate signaling activity in cells.

Figure 8A:
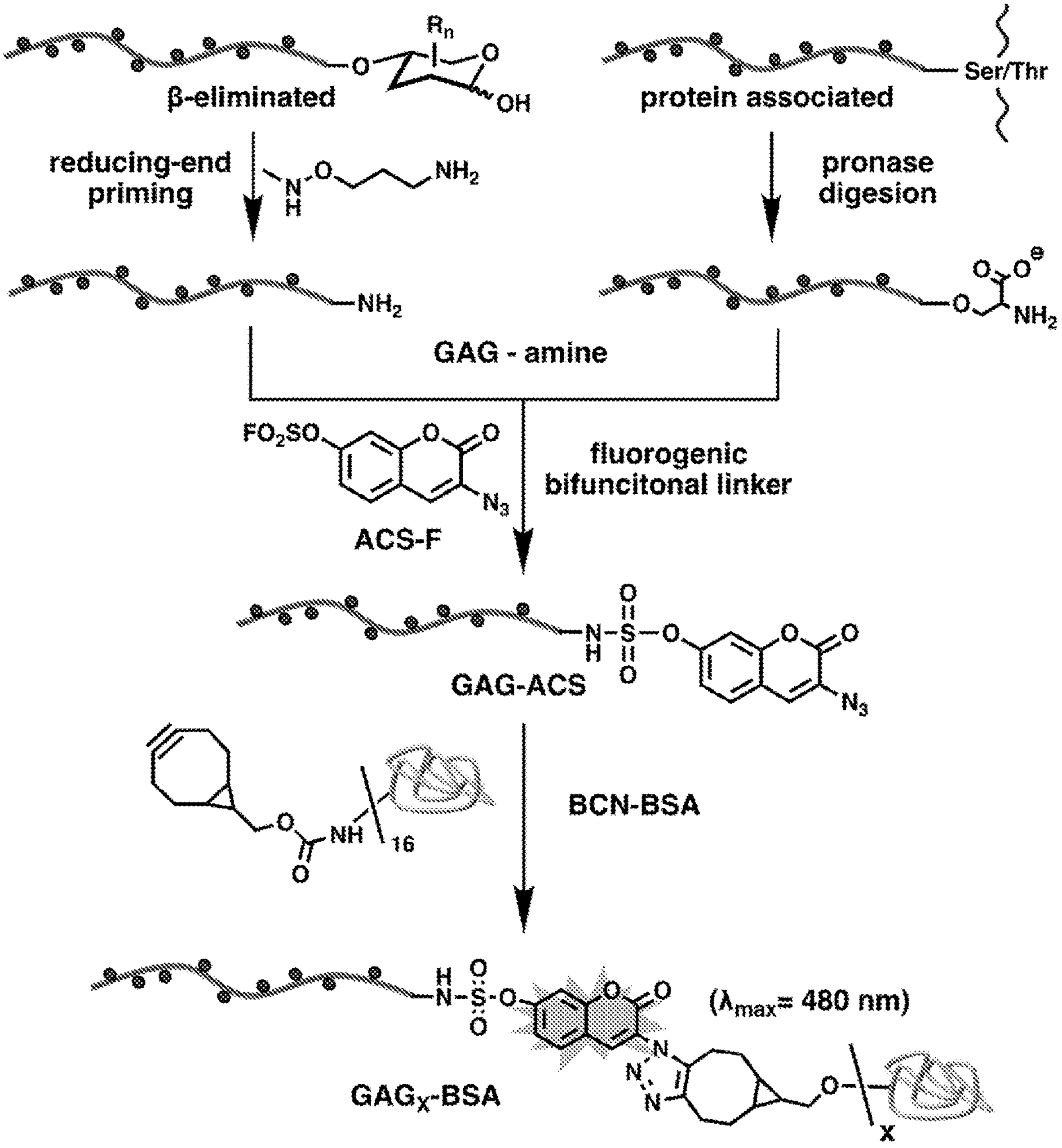
FIGS. 8A-C illustrate the preparation of HS, CS, KS, & HA neoPGs.
Figure 8B:
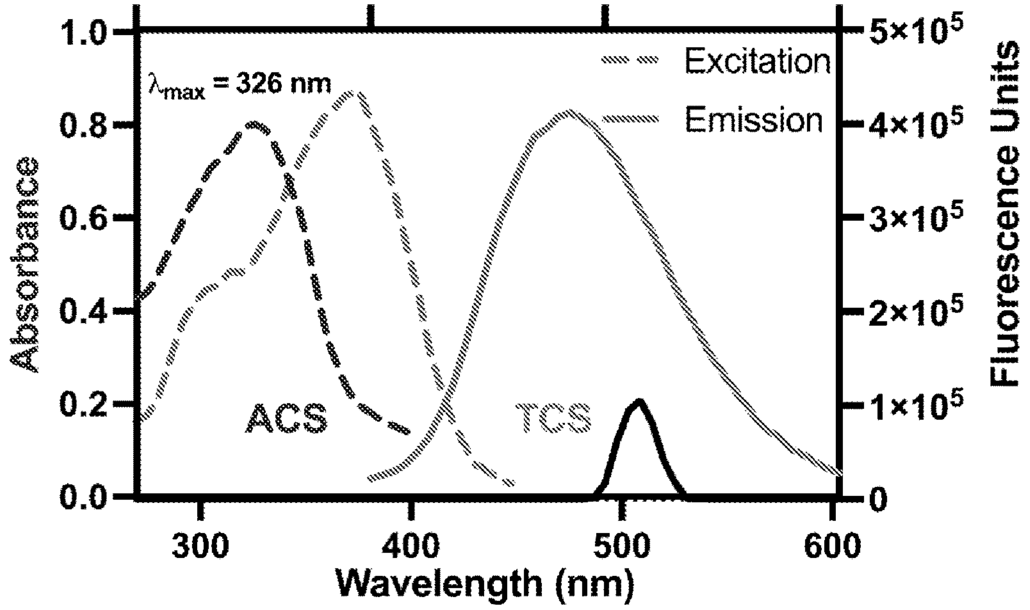

GAG polysaccharide chains can be bound through their reducing ends to a BSA protein carrier with a fluorogenic bioorthogonal linker strategy (FIG. 8A). In this process, the GAG chains are furnished with a novel azido-coumarin linker that produces fluorescent light emission ($\lambda_{ex/em}$=393/477 nm) upon further conjugation with alkynes. This strategy enables direct monitoring and quantification of the coupling reaction (FIG. 8B). The linker is introduced via the sulfur (IV) fluoride exchange (SufEx) reaction between 3-azidocoumarin-7-sulfonyl fluoride (ACS-F) and amine-terminated GAG chains. The amine groups either originate from amino acid residues retained after GAG release from proteoglycans by pronase digestion, in the case of tissue-derived GAGs, or are introduced quantitatively to the hemiacetal end of β-eliminated chains by treatment with N-methylaminooxy propylamine for recombinant and commercial GAGs.

After removal of excess ACS-F linker by size exclusion chromatography and dialysis, the chemically primed GAGs (ACS-GAGs) were conjugated to a bicyclo[6.1.0]nonyne-modified BSA protein (BCN-BSA) via the strain-promoted azide-alkyne cycloaddition (SPAAC) to generate neoPGs (FIG. 8A). Fluorescence readout from the fluorogenic linker provided conjugation kinetics and stoichiometry of the resulting neoPGs, which was confirmed through a combination of BCA and carbazole assays to determine the respective BSA and GAG content after removal of unreacted GAG chains by dialysis. The fluorescence from triazole-coumarin sulfonyl-BSA (TCS-BSA) conjugate produced by reacting BCN-BSA with the ACS-F linker alone was used to calibrate the measurement and to establish the maximal number of conjugation sites (~16 cyclooctynes per BSA) on the protein (FIG. 8B).

Using this approach, neoPG conjugates were prepared using polysaccharides representing the main classes of GAGs. These included commercially available heparin (Hep, a highly sulfated form of HS), HA, and bovine cartilage CS as well as HS, CS and KS isolated from pig lung and mouse liver tissues. Under optimized conditions, BCN-BSA (~1 nM) was reacted with ACS-GAGs (~20 equiv. per BSA) in PBS buffer at ambient temperature for 20 hrs. Each neoPG was assigned a descriptor GAGx-BSA, where x designates the number of GAG chains per BSA molecule. The conjugation process was efficient, and the maximum number of GAG chains introduced into the neoPGs ranged from x~6-8 for HS, KS and HA and x~8-12 for CS. Both the size and charge of the polysaccharides likely contribute to the overall efficiency of the conjugation process; however, we did not observe any noticeable trends. The heparan sulfate mimetic of the conjugates with respect to GAG chain valency can be tuned by controlling the reagent stoichiometry or reaction time.

Figure 8C:
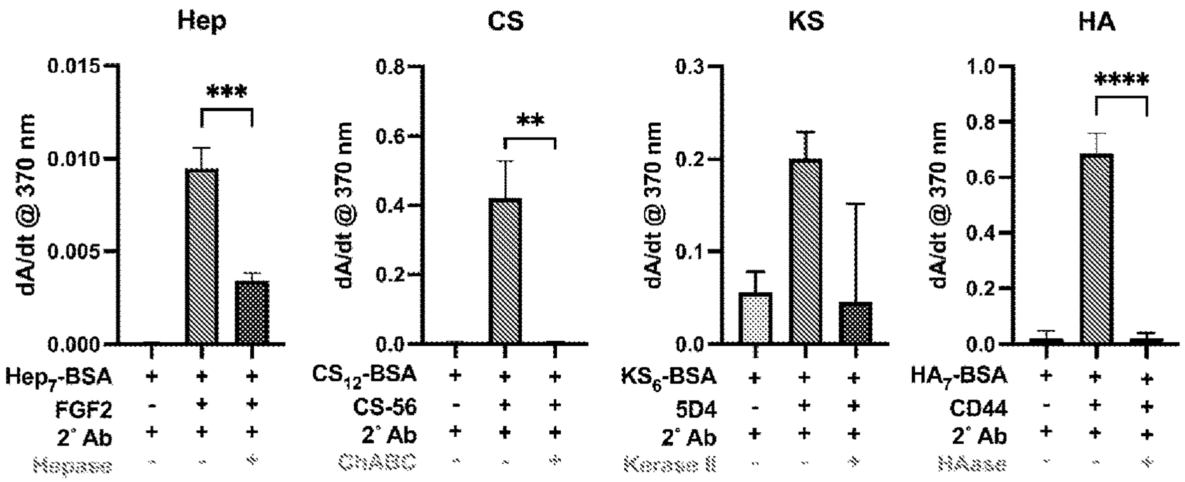

To confirm that the neoPG conjugates retained the protein binding specificities of their parent GAGs after immobilization, we arrayed Hepx-, CSx-, KSx-, and HAx-BSA (100 ng/well) and tested them with proteins and antibodies with known binding activities against these GAGs, i.e., FGF2, CS-56, 5D4 and CD44, respectively (FIG. 8C). Degradation of the GAG chains with HS-, CS-, KS- and HA-specific glycosidase enzymes reduced the binding of these proteins to the neoPGs, further confirming glycan-dependent interactions.

The following statements are intended to describe and summarize various embodiments of the invention according to the foregoing description in the specification.

Statements

1. A method of increasing glucose uptake by differentiated adipocytes comprising:
   incubating pre-adipocytes with a heparan sulfate (HS) mimetic comprising a polymer backbone comprising sulfated disaccharides, the polymer backbone linked to a cell membrane anchoring portion.
2. The method of statement 2, wherein the polymer backbone comprises heparan sulfate glycosaminoglycan disaccharides.
3. The method of statement 3, wherein each heparan sulfate glycosaminoglycan disaccharide is monosulfated, disulfated or trisulfated.
4. The method of statement 2, wherein the polymer backbone comprises poly(acrylamide).
5. The method of statement 4, wherein the poly(acrylamide) comprises approximately one hundred to approximately three hundred acrylamide monomers.
6. The method of statement 4, wherein approximately 40% to approximately 75% of acrylamide monomers in the poly(acrylamide) are modified with heparan sulfate glycosaminoglycan disaccharides.
7. The method of statement 2, wherein the heparan sulfate glycosaminoglycan disaccharides have N-, 2-O, 3-O, and 6-O sulfation.
8. The method of statement 6, wherein the heparan sulfate glycosaminoglycan disaccharides have N-, 2-O, 3-O, and 6-O sulfation.
9. The method of statement 1, wherein the cell membrane anchoring portion is an aptamer that binds to a molecule on a surface of a cell membrane.
10. The method of statement 9, wherein the aptamer binds a cell surface protein that is present on the cell surface of pre-adipocytes in greater quantity as compared to differentiated adipocytes.
11. The method of statement 10, wherein the aptamer binds PDGFα or adipomectin.

12. The method of statement 9, wherein the polymer backbone and the aptamer are each linked to a protein core.

13. The method of statement 12, wherein the polymer backbone is linked to biotin, the aptamer is linked to biotin, and the protein core is streptavidin.

14. The method of statement 1, wherein the cell membrane anchoring portion is a hydrophobic anchor that incorporates into a cell membrane.

15. The method of statement 14, wherein the hydrophobic anchor comprises 1,2-dihexadecanoyl-sn-glycero-3-phosphoethanolamine (DPPE).

16. The method of statement 15, further comprising a fluorophore linked to an end of the polymer backbone opposite to the hydrophobic lipid anchor.

17. The method of statement 14, wherein the hydrophobic anchor comprises cholesterylamine, ceramides, or glycerolipids.

18. The method of statement 1, wherein the heparan sulfate (HS) mimetic is incubated with liposomes before incubation with pre-adipocytes.

19. The method of statement 1, wherein the pre-adipocytes are incubated with the HS mimetic for one hour at 37° C.

20. The method of statement 19, wherein the incubation is daily for three days at a beginning of differentiation of the pre-adipocytes into mature adipocytes.

21. The method of statement 14, wherein the hydrophobic anchor inserts into a glycocalyx of the pre-adipocytes.

22. The method of statement 21, wherein the insertion of the hydrophobic anchor of the HS mimetic into the glycocalyx of the pre-adipocytes increases the glucose clearance capacity of adipocytes that differentiate from the pre-adipocytes as compared to the glucose clearance capacity of adipocytes that differentiate from pre-adipocytes without the HS mimetic.

23. The method of statement 22, wherein the adipocytes that differentiate from the pre-adipocytes incubated with the HS mimetic exhibit approximately 20% increased glucose uptake compared to adipocytes that differentiate from pre-adipocytes that were not incubated with the HS mimetic.

24. The method of statement 22, wherein the adipocytes that differentiate from the pre-adipocytes exhibit more than 20% increased glucose uptake compared to adipocytes that differentiate from pre-adipocytes without the HS mimetic.

25. The method of statement 1, wherein the heparan sulfate mimetic has the formula:

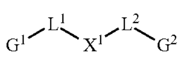

wherein $G^1$ comprises the sulfated disaccharides;

$L^1$ and $L^2$ are each linkers;

$X^1$ is a polymer; and $G^2$ is the cell membrane anchoring portion.

26. The method of statement 25, wherein $G^1$ comprises groups of the formula

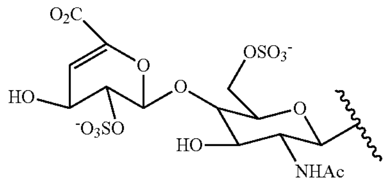

or

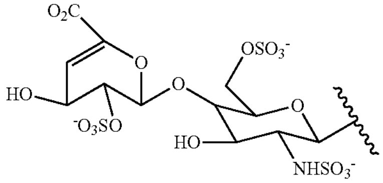

wherein the wavy line represents the point of attachment of $G^1$ to $L^1$.

27. The method of statement 25, wherein $X^1$ is a poly (acrylamide).

28. The method of statement 27, wherein the polyacrylamide is a polyacrylamide of the formula:

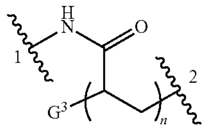, wherein $G^3$ is a reporter group or is absent;

the wavy line with the numeral 1 represents the point of attachment to $L^1$ and the wavy line with the numeral 2 represents the point of attachment to $L^2$.

29. The method of statement 25, wherein $L^1$ is an alkyl or an alkyl-O— group.

30. The method of statement 25, wherein $L^2$ comprises an amido group of the formula $-G^4-C(O)N—$, wherein $G^4$ represents an alkyl group.

31. The method of statement 30, wherein $L^2$ further comprises a group of the formula $-G^4-OP(O)_2O—$.

32. The method of statement 25, wherein $G^2$ is a lipid, an aptamer, an antibody, an antibody fragment or a protein.

33. The method of statement 1, wherein the heparan sulfate mimetic has the formula:

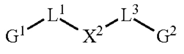

wherein $G^1$ comprises the sulfated disaccharides;

$L^1$ is a linker;

$L^3$ is a linker or absent;

$X^2$ comprises a protein; and $G^2$ is the cell membrane anchoring portion.

34. The method of statement 33, wherein $X^2$ comprises streptavidin bound to biotin groups conjugated to $L^1$ and $L^3$.

35. The method of statement 34, wherein $X^2$ is a group of the formula $—X^3-G^5-X^4—$, wherein $X^3$ and $X^4$ each represent a biotin group and $G^5$ represents streptavidin.

36. The method of statement 33, wherein $G^2$ is a lipid, an aptamer, an antibody, an antibody fragment or a protein.

37. The method of statement 1, wherein the heparan sulfate mimetic has the formula:

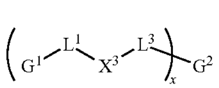

wherein $G^1$ comprises the sulfated disaccharides;
$L^1$ is a linker;
$L^3$ is a linker;
$X^3$ is absent or a reporter;
$G^2$ is the cell membrane anchoring portion; and
x is an integer from 2 to 20.

38. The method of statement 37, wherein the sulfated disaccharides comprise sulfated glycosaminoglycan (GAG).

39. The method of statement 37, wherein the reporter is an azido-coumarin sulfonyl fluoride (ACS-F) linker.

40. The method of statement 37, wherein $L^3$ is a click-chemistry-derived linker.

41. The method of statement 40, wherein $L^3$ is bicyclo[6.1.0]nonyne.

42. The method of statement 37, wherein $G^2$ comprises a lipid, an aptamer, an antibody, an antibody fragment or a protein.

43. A heparan sulfate mimetic for targeting pre-adipocytes and adipocytes having the formula:
a polymer backbone comprising sulfated disaccharides, the polymer backbone
linked to a cell membrane anchoring portion,
wherein the heparan sulfate mimetic associates with the cell membrane or
binds to membrane surface proteins of the pre-adipocytes and the adipocytes; and
the heparan sulfate mimetic has the formula:

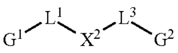

wherein $G^1$ comprises the sulfated disaccharides;
$L^1$ is a linker;
$L^3$ is a linker or absent;
$X^2$ comprises a protein;
$G^2$ is the cell membrane anchoring portion.

44. The heparan sulfate mimetic of statement 43, wherein $X^2$ comprises streptavidin bound to biotin groups conjugated to $L^1$ and $L^3$.

45. The heparan sulfate mimetic of statement 44, wherein $X^2$ is a group of the formula —$X^3$-$G^5$-$X^4$—, wherein $X^3$ and $X^4$ each represent a biotin group and $G^5$ represents streptavidin.

46. The heparan sulfate mimetic of statement 43, wherein $G^2$ is a lipid, an aptamer, an antibody, an antibody fragment or a protein.

47. The heparan sulfate mimetic of statement 43, wherein the sulfated disaccharides comprise heparan sulfate glycosaminoglycan disaccharides.

48. The heparan sulfate mimetic of statement 47, wherein each heparan sulfate glycosaminoglycan disaccharide is monosulfated, disulfated or trisulfated.

49. The heparan sulfate mimetic of statement 48, wherein the heparan sulfate glycosaminoglycan disaccharides comprise at least one of N-, 2-O, 3-O, and 6-O sulfation.

50. The heparan sulfate mimetic of statement 43, wherein the heparan sulfate glycosaminoglycan disaccharides comprise at least one of N-, 2-O, 3-O, and 6-O sulfation.

51. The heparan sulfate mimetic of statement 43, wherein the polymer backbone is linear or branched.

52. The heparan sulfate mimetic of statement 43, wherein the cell membrane anchor is an aptamer that binds to a molecule on a surface of a cell membrane.

53. The heparan sulfate mimetic of statement 52, wherein the aptamer binds a cell surface protein that is present on the cell surface of pre-adipocytes in greater quantity as compared to differentiated adipocytes.

54. The heparan sulfate mimetic of statement 53, wherein the aptamer binds PDGFα or adipomectin.

55. The heparan sulfate mimetic of statement 52, wherein the polymer backbone and the aptamer are each linked to a protein core, wherein each protein core is linked to at least one polymer backbone and at least one aptamer.

56. The heparan sulfate mimetic of statement 55, wherein the polymer backbone is linked to biotin, the aptamer is linked to biotin, and the protein core is streptavidin.

57. The heparan sulfate mimetic of statement 43, wherein the cell membrane anchoring portion is a hydrophobic anchor that incorporates into a cell membrane.

58. The heparan sulfate mimetic of statement 57, wherein the hydrophobic anchor comprises 1,2-dihexadecanoyl-sn-glycero-3-phosphoethanolamine (DPPE).

59. The heparan sulfate mimetic of statement 57, wherein the hydrophobic anchor comprises cholesterylamine, ceramides, or glycerolipids.

60. The heparan sulfate mimetic of statement 43, wherein the heparin sulfate mimetic is further comprises liposomes, wherein the hydrophobic anchor is incorporated into a membrane of the liposomes.

61. A heparan sulfate mimetic for targeting pre-adipocytes and adipocytes having the formula:
a polymer backbone comprising sulfated disaccharides, the polymer backbone
linked to a cell membrane anchoring portion,
wherein the heparan sulfate mimetic associates with the cell membrane or
binds to membrane surface proteins of the pre-adipocytes and the adipocytes; and
wherein the heparan sulfate mimetic has the formula:

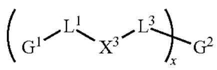

wherein $G^1$ comprises the sulfated disaccharides;
$L^1$ is a linker;
$L^3$ is a linker;
$X^3$ is absent or a reporter;
$G^2$ is the cell membrane anchoring portion; and
x is an integer from 2 to 20.

62. The heparan sulfate mimetic of statement 61, wherein the sulfated disaccharides comprise sulfated glycosaminoglycan (GAG).

63. The heparan sulfate mimetic of statement 61, wherein the reporter comprises an azido-coumarin sulfonyl fluoride (ACS-F) linker.

64. The heparan sulfate mimetic of statement 61, wherein $L^3$ is a click-chemistry-derived linker.
65. The heparan sulfate mimetic of statement 64, wherein $L^3$ comprises bicyclo[6.1.0]nonyne.
66. The heparan sulfate mimetic of statement 61, wherein $G^2$ comprises a lipid, an aptamer, an antibody, an antibody fragment or a protein.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention.

The invention illustratively described herein suitably can be practiced in the absence of any element or elements, or limitation or limitations, which is not specifically disclosed herein as essential. The methods and processes illustratively described herein suitably can be practiced in differing orders of steps, and the methods and processes are not necessarily restricted to the orders of steps indicated herein or in the claims.

Under no circumstances can the patent be interpreted to be limited to the specific examples or embodiments or methods specifically disclosed herein. Under no circumstances can the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method of increasing glucose uptake by differentiated adipocytes comprising:

incubating pre-adipocytes with a heparan sulfate (HS) mimetic comprising a polymer backbone comprising sulfated disaccharides, the polymer backbone linked to a cell membrane anchoring portion.

2. The method of claim 1, wherein the polymer backbone comprises heparan sulfate glycosaminoglycan disaccharides or the cell membrane anchoring portion is a hydrophobic anchor that incorporates into a cell membrane and wherein the polymer backbone optionally comprises poly(acrylamide).

3. The method of claim 2, wherein each heparan sulfate glycosaminoglycan disaccharide is monosulfated, disulfated or trisulfated or have N-, 2-O, 3-O, and 6-O sulfation.

4. The method of claim 1, wherein the cell membrane anchoring portion is an aptamer that binds a cell surface protein that is present on the cell surface of pre-adipocytes in greater quantity as compared to differentiated adipocytes.

5. The method of claim 2, wherein the hydrophobic anchor comprises 1,2-dihexadecanoyl-sn-glycero-3-phosphoethanolamine (DPPE), cholesterylamine, ceramides, or glycerolipids.

6. The method of claim 1, wherein the heparan sulfate (HS) mimetic is incubated with liposomes before incubation with pre-adipocytes for each day for three days at a beginning of differentiation of the pre-adipocytes into mature adipocytes.

7. The method of claim 2, wherein the hydrophobic anchor inserts into a glycocalyx of the pre-adipocytes to increase the glucose clearance capacity of adipocytes that differentiate from the pre-adipocytes incubated with the HS mimetic by approximately 20% increased glucose uptake as compared to the glucose clearance capacity of adipocytes that differentiate from pre-adipocytes without the HS mimetic.

8. The method of claim 1, wherein the heparan sulfate mimetic has the formula:

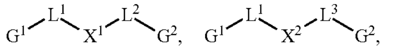
or
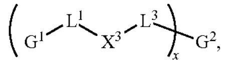

wherein $G^1$ comprises the sulfated disaccharides, wherein the sulfated disaccharides optionally comprise groups of the formula;

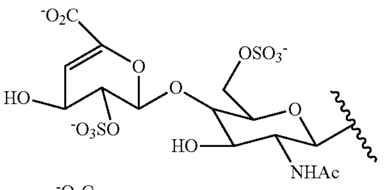
or
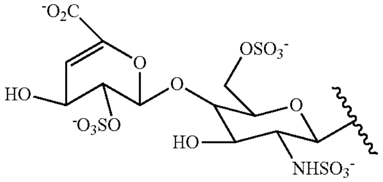
, wherein the wavy line represents the point of attachment of $G^1$ to $L^1$;

$L^1$ and $L^2$ are each linkers;

$L^3$ is a linker or absent;

$X^1$ is a polymer;

$X^2$ comprises a protein;

$X^3$ is absent or a reporter;

$G^2$ is the cell membrane anchoring portion; and x is an integer from 2 to 20.

9. The method of claim 8, wherein;

$X^1$ is a poly(acrylamide), $L^1$ is an alkyl or an alkyl-O— group, $L^2$ comprises an amido group of the formula $-G^4-C(O)N—$, wherein $L^2$ optionally further comprises a group of the formula $-G^4-OP(O)_2O—$ or $G^2$ is a lipid, an aptamer, an antibody, an antibody fragment or a protein, or a combination thereof, wherein $G^4$ represents an alkyl group.

10. The method of claim 9, wherein the polyacrylamide is a polyacrylamide of the formula:

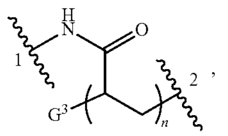

wherein $G^3$ is a reporter group or is absent; and the wavy line with the numeral 1 represents the point of attachment to $L^1$ and the wavy line with the numeral 2 represents the point of attachment to $L^2$.

11. The method of claim 8, wherein:

$X^2$ comprises streptavidin bound to biotin groups conjugated to $L^1$ and $L^3$, $G^2$ is a lipid, an aptamer, an antibody, an antibody fragment or a protein, or $X^2$ is a group of the formula —$X^3$-G-$X^4$—, wherein $X^3$ and $X^4$ each represent a biotin group and $G^5$ represents streptavidin, or a combination thereof.

12. The method of claim 8, wherein;

the sulfated disaccharides comprise sulfated glycosaminoglycan (GAG), the reporter is an azido-coumarin sulfonyl fluoride (ACS-F) linker, or $G^2$ comprises a lipid, an aptamer, an antibody, an antibody fragment or a protein, or $L^3$ is a click-chemistry-derived linker, or a combination thereof.

13. A heparan sulfate mimetic for targeting pre-adipocytes and adipocytes having the formula: a polymer backbone comprising sulfated disaccharides, the polymer backbone linked to a cell membrane anchoring portion, wherein the heparan sulfate mimetic associates with the cell membrane or binds to membrane surface proteins of the pre-adipocytes and the adipocytes; and the heparan sulfate mimetic has the formula:

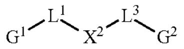

wherein $G^1$ comprises the sulfated disaccharides;

$L^1$ is a linker;

$L^3$ is a linker or absent;

$X^2$ comprises a protein;

$G^2$ is the cell membrane anchoring portion, which is an aptamer, an antibody, an antibody fragment or a protein that selectively targets pre-adipocytes or adipocytes.

14. The heparan sulfate mimetic of claim 13, wherein: $X^2$ comprises streptavidin bound to biotin groups conjugated to $L^1$ and $L^3$ or $X^2$ is a group of the formula —$X^3$-$G^3$-$X^4$, wherein $X^3$ and $X^4$ each represent a biotin group and $G^5$ represents streptavidin, the sulfated disaccharides comprise heparan sulfate glycosaminoglycan disaccharides, or each heparan sulfate glycosaminoglycan disaccharide is monosulfated, disulfated or trisulfated, or comprises at least one of N-, 2-0, 3-0, and 6-0 sulfation, or a combination thereof.

15. The heparan sulfate mimetic of claim 13, wherein the cell membrane anchoring portion is an aptamer that binds a cell surface protein that is present on the cell surface of pre-adipocytes in greater quantity as compared to differentiated adipocytes.

16. The heparan sulfate mimetic of claim 15, wherein: the aptamer binds PDGFα or adipomectin, the polymer backbone and the aptamer are each linked to a protein core, wherein each protein core is linked to at least one polymer backbone and at least one aptamer.

17. The heparan sulfate mimetic of claim 16, wherein the polymer backbone is linked to biotin, the aptamer is linked to biotin, and the protein core is streptavidin.

18. The heparan sulfate mimetic of claim 13, wherein the heparin sulfate mimetic further comprises liposomes.

19. A heparan sulfate mimetic for targeting pre-adipocytes and adipocytes having the formula: a polymer backbone comprising sulfated disaccharides, the polymer backbone linked to a cell membrane anchoring portion, wherein the heparan sulfate mimetic associates with the cell membrane or binds to membrane surface proteins of the pre-adipocytes and the adipocytes; and wherein the heparan sulfate mimetic has the formula:

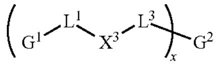

wherein $G^1$ comprises the sulfated disaccharides;

$L^1$ is a linker;

$L^3$ is a linker;

$X^3$ is absent or a reporter;

$G^2$ is the cell membrane anchoring portion, which is an aptamer, an antibody, an antibody fragment or a protein that selectively targets pre-adipocytes or adipocytes; and x is an integer from 2 to 20.

20. The heparan sulfate mimetic of claim 19, wherein: the sulfated disaccharides comprise sulfated glycosaminoglycan (GAG), the reporter comprises an azido-coumarin sulfonyl fluoride (ACS-F) linker, or $L^3$ is a click-chemistry-derived linker, or a combination thereof.

* * * * *

SEQUENCE LISTING

```
<160> NUMBER OF SEQ ID NOS: 12

<210> SEQ ID NO 1
<211> LENGTH: 49
<212> TYPE: DNA
<213> ORGANISM: Artificial Sequence
<220> FEATURE:
<223> OTHER INFORMATION: A synthetic sequence

<400> SEQUENCE: 1

aggtcagatg aggaggggga cttaggactg ggtttatgac ctatgcgtg                49


<210> SEQ ID NO 2
<211> LENGTH: 49
<212> TYPE: DNA
<213> ORGANISM: Artificial Sequence
<220> FEATURE:
<223> OTHER INFORMATION: A synthetic sequence

<400> SEQUENCE: 2

aggtcagatg gtggattcga agtgggagat gcgagtgtac ctatgcgtg                49


<210> SEQ ID NO 3
<211> LENGTH: 25
<212> TYPE: DNA
<213> ORGANISM: Artificial Sequence
<220> FEATURE:
<223> OTHER INFORMATION: A synthetic sequence

<400> SEQUENCE: 3

caatggttgg gaaggaaaag ggcta                                          25


<210> SEQ ID NO 4
```

-continued

<211> LENGTH: 23
<212> TYPE: DNA
<213> ORGANISM: Artificial Sequence
<220> FEATURE:
<223> OTHER INFORMATION: A synthetic sequence

<400> SEQUENCE: 4
gtaggcgcca atgaggaacc gtc 23

<210> SEQ ID NO 5
<211> LENGTH: 24
<212> TYPE: DNA
<213> ORGANISM: Artificial Sequence
<220> FEATURE:
<223> OTHER INFORMATION: A synthetic sequence

<400> SEQUENCE: 5
acacccgaga tttccttcaa actg 24

<210> SEQ ID NO 6
<211> LENGTH: 25
<212> TYPE: DNA
<213> ORGANISM: Artificial Sequence
<220> FEATURE:
<223> OTHER INFORMATION: A synthetic sequence

<400> SEQUENCE: 6
ccatctaggg ttatgatgct cttca 25

<210> SEQ ID NO 7
<211> LENGTH: 21
<212> TYPE: DNA
<213> ORGANISM: Artificial Sequence
<220> FEATURE:
<223> OTHER INFORMATION: A synthetic sequence

<400> SEQUENCE: 7
gaagctgcgg tacaattcca g 21

<210> SEQ ID NO 8
<211> LENGTH: 21
<212> TYPE: DNA
<213> ORGANISM: Artificial Sequence
<220> FEATURE:
<223> OTHER INFORMATION: A synthetic sequence

<400> SEQUENCE: 8
ccccttgtac ccttcaccaa t 21

<210> SEQ ID NO 9
<211> LENGTH: 18
<212> TYPE: DNA
<213> ORGANISM: Artificial Sequence
<220> FEATURE:
<223> OTHER INFORMATION: A synthetic sequence

<400> SEQUENCE: 9
gcatggtgcc ttcgctga 18

<210> SEQ ID NO 10
<211> LENGTH: 22
<212> TYPE: DNA
<213> ORGANISM: Artificial Sequence
<220> FEATURE:
<223> OTHER INFORMATION: A synthetic sequence

<400> SEQUENCE: 10

-continued

```
tggcatctct gtgtcaacca tg                                          22


<210> SEQ ID NO 11
<211> LENGTH: 19
<212> TYPE: DNA
<213> ORGANISM: Artificial Sequence
<220> FEATURE:
<223> OTHER INFORMATION: A synthetic sequence

<400> SEQUENCE: 11

tggacaagaa cagcaacga                                              19


<210> SEQ ID NO 12
<211> LENGTH: 19
<212> TYPE: DNA
<213> ORGANISM: Artificial Sequence
<220> FEATURE:
<223> OTHER INFORMATION: A synthetic sequence

<400> SEQUENCE: 12

aatctcctag tcctggctg                                              19
```